United States Patent [19] [11] 4,024,174
Hayashi et al. [45] May 17, 1977

[54] TRANES-DELTA 2-PROSTAGLANDINS

[75] Inventors: Masaki Hayashi; Seiji Kori; Hirohisa Wakatsuka, all of Takatsuki; Yoshitaka Konishi, Takarazuka, all of Japan

[73] Assignee: Ono Pharmaceutical Company, Osaka, Japan

[22] Filed: Dec. 19, 1964

[21] Appl. No.: 534,509

[30] Foreign Application Priority Data

Dec. 25, 1973 Japan ............................ 48-143738
Dec. 29, 1973 Japan ............................. 49-3726

[52] U.S. Cl. ...................... 260/468 D; 260/240 R; 260/345.7; 260/345.8; 260/347.3; 260/347.9; 260/470; 260/473 A; 260/514 D; 424/305; 424/308; 260/520 B; 424/317
[51] Int. Cl.² ...................................... C07C 177/00
[58] Field of Search .................... 260/468 D, 514 D

[56] References Cited

FOREIGN PATENTS OR APPLICATIONS 817,383  1/1975  Belgium ........................... 260/468
2,261,496  6/1973  Germany ........................... 260/468

OTHER PUBLICATIONS

Nelson, J. Med. Chem. 17, 913 (1974).

*Primary Examiner*—Robert Gerstl
*Attorney, Agent, or Firm*—Albert H. Graddis; Frank S. Chow

[57] ABSTRACT

Trans-Δ² -prostaglandin compounds are disclosed of the formula:

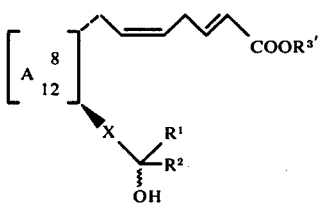

wherein A represents a grouping of the formula:

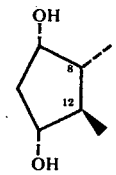

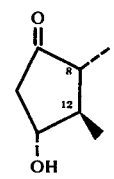

or

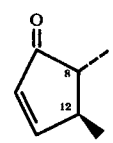

$R^1$ represents an alkyl group containing from 1 to 10 carbon atoms, or an alkyl group containing from 1 to 6 carbon atoms carrying a phenyl substituent or a cycloalkyl substituent of 5 to 7 carbon atoms, $R^2$ represents a hydrogen atom or an alkyl group containing from 1 to 4 carbon atoms, and $R^{3'}$ represents a hydrogen atom or an alkyl group containing from 1 to 12 carbon atoms, the double bonds in the 2- and 5-positions being in the trans- and cis-configurations respectively. These compounds are indicated in the management of conditions such as autoimmune conditions, e.g. rheumatoid arthritis.

13 Claims, No Drawings

TRANES-DELTA 2-PROSTAGLANDINS

This invention is concerned with trans-$\Delta^2$-prostaglandin compounds.

It is an object of the present invention to provide a new process for the preparation of trans-$\Delta^2$-prostaglandin compounds of the general formula:

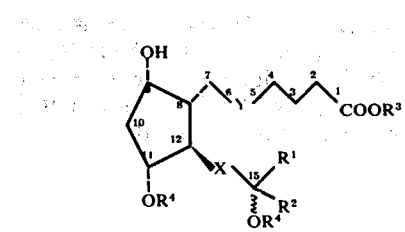

I wherein $R^1$ represents an alkyl group containing from 1 to 10, preferably 5, carbon atoms, or an alkyl group containing from 1 to 6 carbon atoms carrying a phenyl substituent or a cycloalkyl substituent of 5 to 7 carbon atoms, $R^2$ represents a hydrogen atom or an alkyl group containing from 1 to 4 carbon atoms, $R^3$ represents an alkyl group containing from 1 to 12 carbon atoms, $R^4$ represents a 2-tetrahydropyranyl group unsubstituted or substituted by at least one alkyl group, or a 2-tetrahydrofuranyl or 1-ethoxyethyl group, X represents ethylene (i.e. —$CH_2CH_2$—) or, preferably, trans-vinylene (i.e., —CH=CH—) and Y represents ethylene or, preferably, cis-vinylene. It is to be understood that (i) the wavy line in general formula I and in other formulae throughout this specification indicates attachment of the group in question in the $\alpha$- or $\beta$- configuration, and (ii) alkyl groups referred to in this specification may, when appropriate, have straight- or branched-chains.

The compounds of general formula I are useful an intermediates for the preparation of therapeutically useful trans-$\Delta^2$-prostaglandins. Those compounds in which Y represents cis-vinylene are novel compounds and as such constitute a feature of the present invention.

Prostaglandins are derivatives of prostanoic acid which has the following formula:

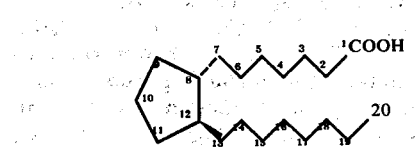

II the dotted line, in accordance with accepted rules of organic nomenclature, denoting the $\alpha$-configuration for the attachment of the group to the cyclopentane ring indicated by the numeral 8, i.e., the group lies behind the general plane of the ring system, and the solid thickened line denoting the $\beta$-configuration where the group lies in front of the plane. Various types of prostaglandins are known, the types depending inter alia on the structure and substituents on the alicyclic ring. For example, the alicyclic rings of prostaglandins F(PGF), E(PGE) and A(PGA) have the structures:

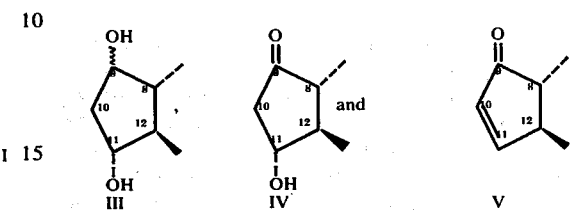

III IV V respectively.

Such compounds are sub-classified according to the position of double (bond(s) in the side chain(s) attached to the 8- and 12-positions of the alicyclic ring. Thus PG-1 -compounds have a trans-double bond between $C_{13}$-$C_{14}$(trans-$\Delta^{13}$), PG-2 -compounds have a cis-double bond between $C_5$-$C_6$ and a trans-double bond between $C_{13}$-$C_{14}$ (cis-$\Delta^5$, trans-$\Delta^{13}$), and PG-3 compounds have cis-double bonds between $C_5$-$C_6$ and $C_{17}$-$C_{18}$ and a trans-double bond between $C_{13}$-$C_{14}$ (cis-$\Delta^5$, trans-$\Delta^{13}$, cis-$\Delta^{17}$). For example, prostaglandin $F_{1\alpha}$(PGF$_{1\alpha}$) and prostaglandin $E_1$ (PGE$_1$) are characterized by the following structures VI and VII.

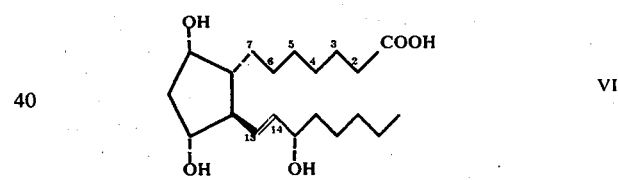

VI and

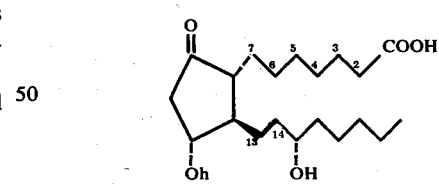

VII respectively. The structures of PGF$_{2\alpha}$ and PGE$_2$, as members of the PG-2 group, correspond to those of formulae VI and VII respectively with a cis-double bond between the carbon atoms in positions 5 and 6. Compounds in which the double bond between the carbon atoms in positions 13 and 14 of members of the PG-1 group is replaced by ethylene are known as dihydro-prostaglandins, e.g. dihydro-prostaglandin-F$_{1\alpha}$- (dihydro-PGF$_{1\alpha}$) and dihydro-prostaglandin-E$_1$ (dihydro-PGE$_1$). When there is a double bond between the carbon atoms in positions 2 and 3 the compounds are known as cis- or trans-$\Delta^2$-prostaglandins.

Moreover, when one or more methylene groups are added to, or eliminated from, the aliphatic group attached to the 12-position of the alicyclic ring of the prostaglandins the compounds are known, in accordance with the usual rules of organic nomenclature, as ω-homo-prostaglandins (methylene group added) or ω-nor-prostaglandins (methylene group eliminated) and, when more than one methylene group is added or eliminated, the number is indicated by di-, tri- etc. before the prefix "homo" or "nor".

Prostaglandins are generally known to possess pharmacological properties, for example they stimulate smooth muscle, hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. PGE$_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammels. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties and new processes for the preparation of therapeutically useful prostaglandins.

A process is known for the preparation of a prostaglandin analogous to PGE$_1$ in which there is a trans double bond between $C_2$-$C_3$, i.e., trans-$\Delta^2$-PGE$_1$, of the formula:

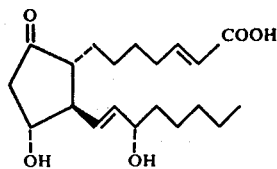

The process, which is described by Van Dorp in Annals New York Academy of Sciences, 180, 185 (1971), is based on a biosynthetic reaction involving incubating sheep seminal vesicular glands with an unsaturated fatty acid as substrate, according to the reaction scheme:

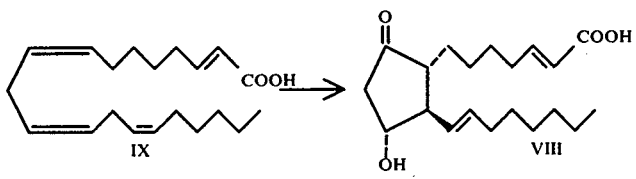

However, this process is difficult and expensive to carry out on a large scale due to the complicated synthesis of the unsaturated fatty acid and the use of expensive materials of animal origin of difficult availability.

In the specification of United States Patent Application 427,403 filed by M. Hayashi et al on 21 December 1973 there is described inter alia a multi-stage process for the preparation of trans-$\Delta^2$-prostaglandins conforming to general formula I wherein Y represents ethylene, but that process involving intermediates of the general formula:

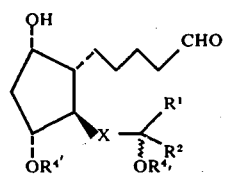

(wherein $R^1$ and $R^2$ are as hereinbefore defined, and $R^{4'}$ represents a 2-tetrahydropyranyl group unsubstituted or substituted by at least one alkyl group or 1-ethoxyethyl group) is inapplicable to the preparation of trans-$\Delta^2$-prostaglandins of formula I wherein symbol Y represents cis-vinylene, e.g. trans-$\Delta^2$-PG-2's.

In the specification of Belgian Patent 792,803 granted to Carlo Erba S.p.A. there is described a process for the preparation of inter alia $\Delta^2$-prostaglandins, but the prostaglandin products therein disclosed are 8,12-diisoprostanoic acids or analogues thereof, i.e., the groups linked to the cyclopentane ring are in inverse configuration vis-a-vis the trans-$\Delta^2$-prostaglandins of general formula I depicted above, i.e., the products disclosed in the Belgian patent have the groupings attached to the 8- and 12-positions of the prostanoic acid structure in $\beta$- and $\alpha$-configurations respectively. The process described in the Belgian patent as applied to $\Delta^2$-prostaglandins would involve the use of Wittig reagents of the general formula:

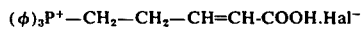    XI (wherein φ represents the phenyl radical and Hal represents a chlorine or bromine atom), which would necessitate as starting materials homoallyl halides of the formula:

    XII (wherein Hal is as hereinbefore defined), which halides have not previously been described in the chemical literature and are known to be difficult to synthesize because of their liability tor release hydrogen halide.

After research and experimentation a new and advantageous process has now been found which can produce trans-$\Delta^2$-prostaglandins of general formula I in which Y is cis-vinylene as well as ethylene, and from such compounds therapeutically useful trans-$\Delta^2$-prostaglandins, a class of which, viz. trans-$\Delta^2$,cis-$\Delta^5$-prostaglandins of the F, E and A series, is entirely novel.

According to the present invention the trans-$\Delta^2$-prostaglandin analogues of general formula I are prepared by the process which comprises reacting a compound of the general formula:

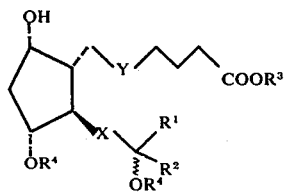    XIII (wherein $R^1$, $R^2$, $R^3$, $R^4$, X and Y are as hereinbefore defined, $R^4$ preferably being the 2-tetrahydropyranyl group) with a compound of the general formula:

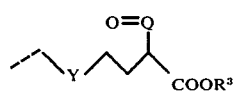    XIV (wherein $R^5$ and $R^6$ each represents an alkyl group containing from 1 to 6 carbon atoms or a cycloalkyl group containing from 3 to 6 carbon atoms) to obtain a lithium esterenolate of the general formula:

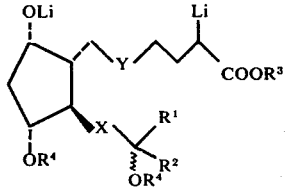    XV (wherein the various symbols are as hereinbefore defined), reacting the lithium esterenolate with benzeneselenenyl bromide (i.e., φSeBr in which φ represents the phenyl radical) or diphenyldiselenide or a dialkyl- or diphenyl-disulfide of the formula $R^7SSR^7$, wherein the symbols $R^7$ both represent alkyl groups containing from 1 to 4 carbon atoms or phenyl radicals, hydrolyzing the resulting intermediate to convert the —OLi group attached to the cyclopentane ring to an α-hydroxy group and to obtain a compound of the general formula:

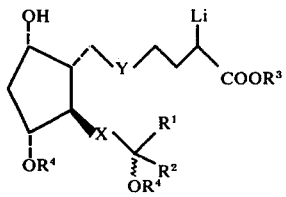    XVI (wherein $R^1$, $R^2$, $R^3$, $R^4$, X and Y are as hereinbefore defined and Q represents -Seφ, in which φ is as hereinbefore defined, or a group —$SR^7$, in which $R^7$ is as hereinbefore defined), treating the resulting compound with hydrogen peroxide or sodium periodate, and decomposing the resulting compound of the general formula:

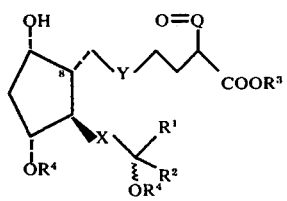    XVII wherein the various symbols are as hereinbefore defined) to convert the grouping

attached to the 8-position of the cyclopentane ring to the trans-$\Delta^2$-grouping

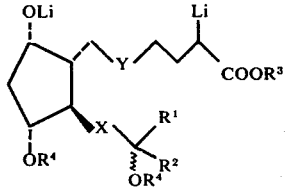

wherein Y and $R^3$ are as hereinbefore defined.

The reaction between the prostaglandin compound of general formula XIII and the lithiated amine of general formula XIV is carried out in an organic solvent medium, for example by adding dropwise a solution of a prostaglandin compound of formula XIII in tetrahydrofuran to a solution of an amine of formula XIV in tetrahydrofuran at a low temperature, e.g. −70° C., the ratio of the molecular equivalents of the compounds of formula XIII to XIV in the reaction mixture being 1:2 to 3. After completion of the addition of the prostaglandin solution, the reaction mixture is stirred at the same temperature for about 30 minutes to obtain a solution of the lithium esterenolate of formula XV.

The reaction between the lithium esterenolate of formula XV and benzeneselenenyl bromide, diphenyldiselenide or dialkyl- or diphenyl-disulphide is preferably carried out in tetrahydrofuran, diethyl ether, hexane or pentane or a mixture of two or more of them, tetrahydrofuran being the preferred solvent medium, at a low temperature, e.g. −70° C. Thus, to the lithium esterenolate solution obtained as described above there is added a solution in tetrahydrofuran of 3 or 4 molecular equivalents of benzeneselenenyl bromide or diphenyl-diselenide, or 2 to 3 molecular equivalents of dialkyl- or diphenyl-disulphide, for each molecular equivalent of lithium esterenolate present, the temperature of the two solutions being −70° C. The reaction mixture is stirred at −70° C. (a) for one hour when a selenium compound is the reactant or (b) for 30 minutes when a disulphide is the reactant, and subsequently at ambient temperature, e.g. 15° C. for 30 minutes. After addition of, for example, a small amount of a saturated aqueous ammonium chloride solution to the solution of the resulting prostaglandin intermediate to hydrolyze the —OLi group attached to the cyclopentane ring to an α-hydroxy group, the product of formula XVI is extracted with ethyl acetate.

When the product of formula XVI is a compound wherein Q is benzeneselenenyl, i.e., -Seφ, the ethyl acetate solution of the product is then treated with 5 to 7 molecular equivalents of hydrogen peroxide at a temperature below 30° C. or with 5 molecular equivalents of sodium periodate in the presence of a lower alkanol, preferably methanol and water, at a temperature below 20° C., preferably for about 24 hours, to form a compound of formula XVII wherein O=Q- is benzeneseleninyl, i.e., —Se(O)φ, and stirring of the reaction mixture at a temperature of 25° to 30° C. for one hour results in decomposition of the compound to a trans-Δ²-prostaglandin analogue of general formula I, which can be separated from the reaction medium by methods known per se and purified by column chromatography in silica gel.

When the product of formula XVI is a compound wherein Q is a group —SR⁷, R⁷ being as hereinbefore defined, the product is separated from the ethyl acetate solution by methods known per se and treated with hydrogen peroxide or sodium periodate in the same way as hereinbefore described for a product of formula XVI wherein Q is benzeneselenenyl to obtain a compound of general formula XVII wherein Q is a group —SR⁷, R⁷ being as hereinbefore defined, which can be separated from the reaction medium by methods known per se.

When the compound of formula XVII is one wherein Q represents an alkylthio group —SR⁷', wherein R⁷' represents an alkyl group containing from 1 to 4 carbon atoms, the compound is dissolved in toluene and the solution stirred, preferably in the presence of a small amount of calcium carbonate, at a temperature of 100° to 120° C. for a period ranging from 5 to 24 hours to decompose the compound to a trans-Δ²-prostaglandin analogue of general formula I. When the compound of general formula XVII is one wherein Q represents the phenylthio group, the compound is dissolved in carbon tetrachloride and the solution stirred, preferably in the presence of a small amount of calcium carbonate, at a temperature of about 50° C. for a period ranging from 5 to 24 hours to decompose the compound to a trans-Δ²-prostaglandin analogue of general formula I. The compounds of general formula I can be separated from the reaction medium by methods known per se and purified by column chromatography on silica gel.

The starting materials of general formula XIII employed in the process of the present invention can be prepared from the corresponding acids of the general formula:

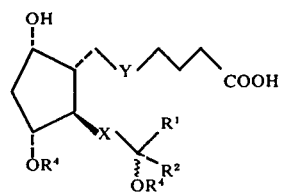

(wherein $R^1$, $R^2$, $R^4$, X and Y are as hereinbefore defined) by reaction with (i) diazoalkane compounds, e.g. diazomethane, (ii) alcohols or thiols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Patents Nos. 1,362,956 and 1,364,125).

Compounds of general formula XVIII may be prepared by reacting a bicyclo-octane derivative of the general formula:

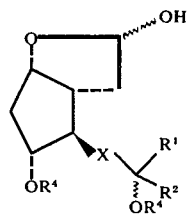

(wherein $R^1$, $R^2$, $R^4$ and X are as hereinbefore defined) with 4-carboxy-n-butylidenetriphenyl-phosphorane of the formula $\phi_3P=CH-(CH_2)_3$-COOH (wherein φ is as hereinbefore defined) to obtain a cyclopentane derivative of the general formula:

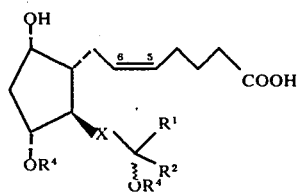

(wherein $R^1$, $R^2$, $R^4$ and X are as hereinbefore defined) and optionally hydrogenating by methods known per se the cis-double bond in the $C_5$-$C_6$ position to obtain a corresponding compound of the general formula:

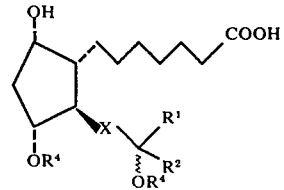

wherein $R^1$, $R^2$, $R^4$ and X are as hereinbefore defined.

If in general formulae XX and XXI X represents a trans-vinylene group, mild reducing conditions should be used for the said optional reduction step in order to reduce only the $C_5$-$C_6$ double bond and not to affect the double bond in X. Suitably the reduction may be effected by hydrogenation in the presence of a hydrogenation catalyst, for example palladium on charcoal, in the presence of an inert organic solvent, for example a lower alkanol, e.g. methanol or ethanol, at laboratory temperature at normal or elevated pressure, e.g. at a hydrogen pressure from atmospheric to 15 kilograms per square centimetre. Advantageously the quantity of hydrogen which reacts is observed during the course of the reaction so that the reaction may be terminated before any reduction of X from trans-vinylene to ethylene occurs.

If in general formula XXI X represents an ethylene group (X representing in general formula XX either trans-vinylene or ethylene), then in the said optional reduction step more rigorous reducing conditions may be used, especially if in general formula XX X represents trans-vinylene, for example hydrogenation in the presence of a hydrogenation catalyst usually used for the hydrogenation of double bonds such as various forms of platinum, palladium or nickel, in a suitable solvent (for example methanol, ethanol, water, dioxan or acetic acid or a mixture of two or more of them), at 0° to 50° C. and at normal or elevated pressure, e.g. at a hydrogen pressure from atmospheric to 15 kilograms per square centimetre.

The reaction between the bicyclo-octanes of general formula XIX and 4-carboxy-n-butylidenetriphenyl-phosphorane [obtained by the reaction of sodio methylsulphinylcarbanide with 4-carboxy-n-butyltriphenylphosphonium bromide] is carried out under the normal conditions utilized for effecting the Wittig reaction, e.g. in an inert solvent at ambient temperature. The reaction is preferably carried out in dimethylsulphoxide because the phosphorane compound is practically insoluble in other solvents, e.g. tetrahydrofuran, and because a cis-double bond must be formed stereospecifically in the Wittig reaction. For the better performance of the Wittig reaction more than two molecular equivalents of the phosphorane compound are required for each mole of the bicyclo-octane reactant. The reaction is generally effected at a temperature of 10°–40° C., preferably at 20°–30° C., and is usually complete after about 30 minutes to four hours at laboratory temperature. The acid product of formula XX may be extracted from the reaction mixture by conventional procedures and further purified by column chromatography on silica gel.

The bicyclo-octane starting materials of general formula XIX wherein X represents ethylene can be prepared by the series of reactions depicted schematically below:

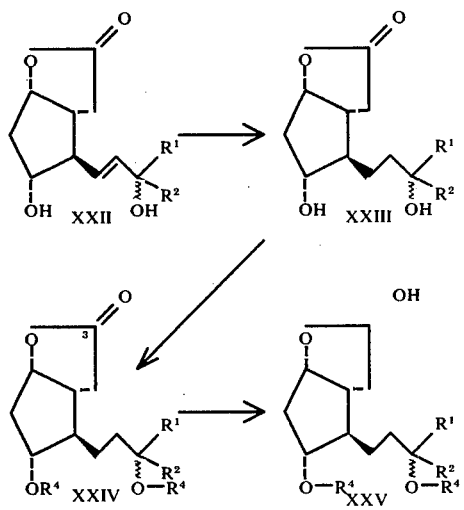

wherein $R^1$, $R^2$ and $R^4$ are as hereinbefore defined.

The compounds of formula XXII are dissolved in a suitable solvent, e.g. methanol or ethanol, and then subjected to catalytic hydrogenation in the presence of a catalyst effective for the reduction of the double bond to ethylene, for example palladium on charcoal, palladium black or platinum dioxide. The resulting compounds of formula XXIII are then reacted with a dihydropyran, dihydrofuran or ethyl vinyl ether in an inert organic solvent, such as methylene chloride, in the presence of a condensing agent, for example p-toluenesulphonic acid, to obtain the compounds of formula XXIV. Those compounds are then reduced at a low temperature, preferably below −50° C., with a reagent capable of reducing the oxo radical in the position indicated as 3 to a hydroxy radical, preferably using diisobutylaluminium hydride.

The bicyclo-octane starting materials of general formula XIX wherein X represents trans-vinylene and those of general formula XXII can be prepared using initially 2-oxa-3-oxo-6-syn-formyl-7-anti-acetoxy-cis-bicyclo[3,3,0]-octane (E. J. Corey et al, J. Amer. Chem. Soc. 91, p. 5675) and applying thereto known procedures [see, for example, J. Amer. Chem. Soc. 92, 397 (1970), J. Amer. Chem. Soc. 92, 2586 (1970) and French Patent 7,215,314 (Publication No. 2134673) and United States Patent Applications 247,803 and 356,248 filed by M. Hayashi et al on 26th April 1972 and 1 May 1973 respectively].

The lithiated amines of general formula XIV employed in the process of the invention, for example lithium diisopropylamide, and benzeneselenenyl bromide and diphenyldiselenide can be prepared by known methods, for example as described in J. Amer. Chem. Soc., 95, 6139 (1973).

The trans-$\Delta^2$-prostaglandin analogues of general formula I obtained by the process of the present invention can be converted into trans-$\Delta^2$-prostaglandins F, E and A having useful pharmacological properties typical of the 'natural' prostaglandins and known analogues thereof by the reactions depicted schematically below:

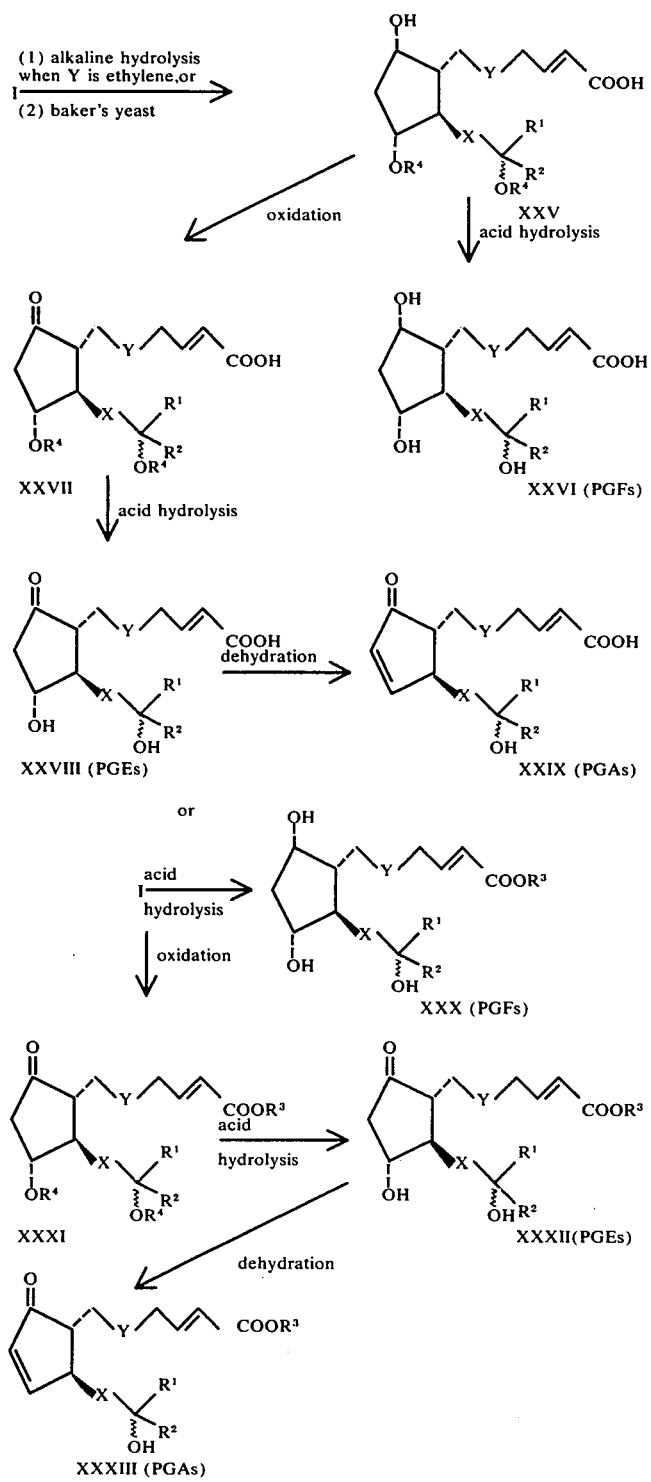

wherein the various symbols are as hereinbefore defined.

The hydrolysis of the alkyl esters of general formula I to the corresponding acids of general formula XXV may be carried out according to methods known per se for example (1) when Y represents ethylene, by treatment of the ester in an inert organic solvent (e.g. tetrahydrofuran) with an aqueous solution of sodium or potassium hydroxide or carbonate, or (2) by means of baker's yeast [cf. C. J. Sih et al, J. Amer. Chem. Soc., 94, 3643 (1972)].

The tetrahydropyranyloxy, tetrahydrofuranyloxy and ethoxyethoxy groups (—OR$^4$) in the compounds of general formulae XXV and XXVII, and I and XXXI, may be converted into hydroxy radicals by mild hydrolysis with an aqueous solution of an organic acid, e.g. acetic acid, or with a dilute inorganic acid, e.g. dilute hydrochloric acid. Advantageously an organic solvent miscible with water, such as tetrahydrofuran or an alcohol, is employed as the starting acids and esters of the aforementioned general formulae are practically insoluble in water. The treatment of the compounds of general formulae XXV, XXVII, I and XXXI may be carried out at a temperature ranging from ambient temperature to 60° C. (preferably at a temperature below 45° C.) with an acid mixture, such as a mixture of acetic acid, water and tetrahydrofuran, or a mixture of hydrochloric acid with tetrahydrofuran or methanol.

The PGF alicyclic ring in the compounds of general formulae XXV and I can be converted into a PGE ring [cf. formulae XXVII and XXXI] by methods known per se for the conversion of a hydroxy group in the 9-position of a prostaglandin to an oxo radical, for example by oxidation with a weak oxidizing agent such as a chromic acid solution (e.g. obtained from chromium trioxide, manganese sulphate, sulphuric acid and water) or Jones' reagent.

The PGE compounds of general formulae XXVIII and XXXII can be converted into corresponding PGA compounds by methods known per se, for example by subjecting the PGE's to dehydration using an aqueous solution of an organic or inorganic acid having a higher concentration than that employed for hydrolysis of compounds of general formulae XXV, XXVII, I and XXXI, e.g. acetic acid or 1N hydrochloric acid, and heating at a temperature of 30°–60° C.

The present invention is concerned with the preparation of all compounds of general formula I in the 'natural' form or its enantiomeric form, or mixtures thereof, more particularly the racemic form consisting of equimolecular mixtures of natural and its enantiomeric form.

As will be apparent to those skilled in the art, the compounds depicted in general formula I have at least five centres of chirality, these five centres of chirality being at the alicyclic ring carbon atoms identified as 8 and 12 and 9 and 11 and at the C-15 carbon atom which has attached to it a group —$OR^4$ wherein $R^4$ is as hereinbefore defined. Still further centres of chirality may occur in branched-chain alkyl groups represented by the symbols $R^1$ and $R^2$. The presence of chirality leads, as is well known, to the existence of isomerism. However, the compounds of general formula I all have such a configuration that the side-chains attached to the ring carbon atoms in the positions identified as 8 and 12 are trans with respect to each other and as depicted, viz. in the α- and β-configurations respectively. Accordingly, all isomers of general formula I, and mixtures thereof, which have those side-chains attached to the ring carbon atoms in positions 8 and 12 in the trans-configuration and have a group —$OR^4$ as depicted in the 15-position are to be considered within the scope of general formula I. Those compounds wherein Y represents cis-vinylene are new compounds.

The trans-$\Delta^2$-PGF, -PGE and -PGA compounds of general formulae XXVI, XXVIII, XXIX, XXX, XXXII and XXXIII, wherein Y represents cis-vinylene and the other symbols are as hereinbefore defined, which are embraced by the general formula:

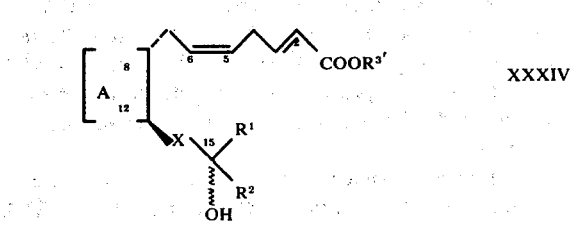

XXXIV

[wherein A represents a grouping of the formula:

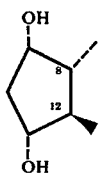

XXXV or of formula IV or V as hereinbefore depicted, $R^1$, $R^2$ and X are as hereinbefore defined, and $R^{3'}$ represents a hydrogen atom or an alkyl group containing from 1 to 12 carbon atoms, the double bonds in the 2- and 5-positions being in the trans- and cis-configurations respectively] are new compounds, and they and cyclodextrin clathrates of such acids and esters, and when $R^{3'}$ represents a hydrogen atom, non-toxic salts thereof, constitute another feature of the invention. It is to be understood that all compounds of general formula XXXIV in the 'natural' form or its enantiomeric form, or mixtures thereof, more particularly the racemic form consisting of equimolecular mixtures of natural and its enantiomeric form, are to be considered as within the present invention. With regard to isomers of general formula XXXIV reference is made to the explanation given hereinbefore concerning isomers of general formula I.

Of particular interest are those compounds of general formula XXXIV, and those of general formulae XXVI, XXVIII, XXIX, XXX, XXXII and XXXIII wherein Y represents cis-vinylene, and the grouping

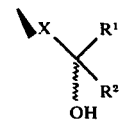

is of the general formula:

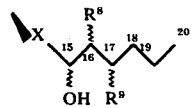

XXXVI wherein X is as hereinbefore defined, and $R^8$ and $R^9$, which may be the same or different, each represents a hydrogen atom or a methyl group, or such a grouping in which $R^8$ and $R^9$ represent hydrogen atoms and the carbon atom in the 15-position carries a methyl group, or the carbon atoms in the 15- and 16-positions each carry a methyl group, or a grouping of the general formula:

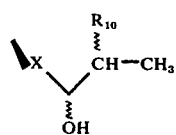

XXXVII wherein X is as hereinbefore defined, and $R^{10}$ represents a phenyl or cyclohexyl radical. Preferably symbol X in general formula XXXIV, XXXVI and XXXVII represents trans-vinylene.

Of outstanding importance are the new compounds trans-$\Delta^2$-PGF$_{2\alpha}$, 15-methyl-trans-$\Delta^2$-PGF$_{2\alpha}$, 16-methyl-trans-$\Delta^2$-PGF$_{2\alpha}$, 17-methyl-trans-$\Delta^2$-PGF$_{2\alpha}$, 15,16-dimethyl-trans-$\Delta^2$-PGF$_{2\alpha}$, 16-phenyl-$\omega$-trinor-trans-$\Delta^2$-PGF$_{2\alpha}$ and 16-cyclohexyl-$\omega$-trinor-trans-$\Delta^2$-PGF$_{2\alpha}$, and the corresponding PGE$_2$ and PGA$_2$ compounds, and methyl esters of all such prostaglandin F$_{2\alpha}$, E$_2$ and A$_2$ compounds. It is to be understood that in the aforesaid compounds the methyl, phenyl and cyclohexyl substituents may have the R- or S-configuration, or be a mixture of R- and S-configurations, preferably a racemic mixture.

The prostaglandins of general formulae XXVI, XXVIII and XXIX, including those prostaglandins of general formula XXXIV wherein R$^{3'}$ represents a hydrogen atom, can be converted into salts or alkyl esters having from 1 to 12 carbon atoms in the alkyl moiety.

The salts may be prepared from the compounds of general formula XXVI, XXVIII and XXIX, by methods known per se, for example by reaction of stoichiometric quantities of acids of the said general formulae and the appropriate base, e.g. an alkali metal hydroxide or carbonate, ammonium hydroxide, ammonia or an amine, in a suitable solvent. The salts may be isolated by concentration of the solution or, if sufficiently insoluble in the reaction medium, by filtration, if necessary after removal of part of the solvent. Preferably the salts are nontoxic salts, i,e., salts the cations of which are relatively innocuous to the animal organism when used in therapeutic doses so that the beneficial pharmacological properties of the prostaglandins of general formula XXVI, XXVIII and XXIX are not vitiated by side-effects ascribable to those cations. Preferably the salts are water-soluble. Suitable salts include the alkali metal, e.g. sodium and potassium, and ammonium salts and pharmaceutically-acceptable (i.e., non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

Alkyl esters of the prostaglandins of general formulae XXVI, XXVIII and XXIX can be obtained by reaction of the acids with (i) diazoalkane compounds, e.g. diazomethane, (ii) alcohols or thiols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Patents Nos. 1,362,956 and 1,364,125).

The prostaglandins of general formulae XXVI, XXVIII and XXIX can also be converted into prostaglandin alcohols, i.e., compounds in which the carboxy radical is replaced by the hydroxymethylene (i.e., —CH$_2$OH) group, conforming to the general formula:

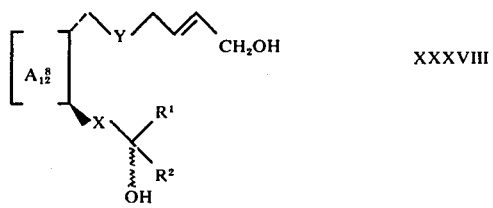

XXXVIII wherein R$^1$, R$^2$, X, Y and A are as hereinbefore defined. Those trans-$\Delta^2$-prostaglandins alcohols of general formula XXXVIII wheerein Y is cis-vinylene are new compounds and as such constitute another feature of the invention.

The trans-$\Delta^2$-prostaglandin alcohols of general formula XXXVIII can be prepared from the corresponding acids by application of the method described by Pike, Lincoln and Schneider in J. Org. Chem. 34, 3,552–3,557 (1969), for example by converting the acids of general formulae XXVI, XXVIII and XXIX into their methyl esters and then the esters into oximes, and reducing the oximes with lithium aluminum hydride to form oxime alcohols, and hydrolyzing them with, for example, acetic acid. PGF alcohols can also be obtained directly by reducing PGF compounds of general formula XXVI or methyl esters thereof with lithium aluminum hydride. The alcohol derivatives of prostaglandins of general formula XXXVIII possess pharmacological properties similar to the acids of general formulae XXVI, XXVIII and XXIX from which they are derived.

The prostaglandins of general formulae XXVI, XXVIII and XXIX and alkyl esters thereof, and corresponding alcohols of general formula XXXVIII may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates, $\alpha$, $\beta$ or $\gamma$-Cyclodextrins or mixtures thereof may be used in the preparation of the cyclodextrin clathrates. Conversion into their cyclodextrin clathrates serves to increase the stability of the prostaglandin compounds.

Prostaglandin compounds of general formula XXVI, XXVIII and XXIX obtained by the process of the present invention and esters and alcohol derivatives thereof, and their cyclodextrin clathrates, and non-toxic salts possess the valuable pharmacological properties typical of prostaglandins in a selective fashion including, in particular, hypotensive activity, inhibitory activity on blood platelet aggregation, inhibitory activity on gastric acid secretion and gastric ulceration and bronchodilator activity and are useful in the treatment of hypertension, in the treatment of disorders of the peripheral circulation, in the prevention and treatment of cerebral thrombosis and myocaridal infarction, in the treatment of gastric ulceration and in the treatment of asthma. Compounds within general formula XXXIV, and when R$^{3'}$ represents a hydrogen atom non-toxic salts thereof, also possess useful immuno-suppressive properties.

The pharmacological properties of specific prostaglandin compounds within general formulae XXVI, XXVIII and XXIX wherein Y represents ethylene, have previously been described in United States Patent Application 427403. For example, in laboratory screening tests, the compound 16(R)-methyl-trans-$\Delta^2$-PGE$_1$ produces: (a) a 26 mm.Hg fall for 11 minutes and a 66 mm.Hg fall for 18 minutes in the blood-pressure of the allobarbital-anaesthetized dog by intravenous administration at doses of 0.05 and 0.20 µg./kg. animal body weight respectively and is 9.5 times as potent as PGE$_1$ in this respect; (b) 50% inhibition of adenosine diphosphate-induced blood platelet aggregation in platelet-rich plasma of rabbits at a dose of $3.1 \times 10^{-2}$ µg./ml. in comparison with controls, the corresponding dose for PGE$_1$ being $8.8 \times 10^{-2}$ µg./ml.; (c) an increase in gastric acid pH from 2.0–2.5 to at least 4.0 in 50% of pentagastrin-treated rats when perfused into the stomach at a rate of 0.12 (confidence limit 0.076–0.190) µg./animal/minute; (d) 23.02% and 31.14% inhibitions of stress ulceration in rats [produced according to the method of Takagi and Okabe - Jap. J. Pharmac. 18, 9–18 (1968)] by oral administration at doses of 2 and 10 µg./kg. animal body weight respectively, and (e) 55.9% and 62.0% inhibitions by intravenous administration at doses of 0.05 and 0.10 µg./kg. animal body weight, respectively, of the increase in resistance in the respiratory tract induced by the administration of histamine to guinea-pigs, as determined by the method of Konzett and Rossler, Arch. exp. Path. Pharmak., 195,71–74 (1940).

Moreover, when trans-$\Delta^2$-PGE$_1$, trans-$\Delta^2$-PGA$_1$, trans-$\Delta^2$-dihydro-PGE$_1$ are administered intravenously to the allobarbital-anaesthetised dog at doses of 1 µg./kg. animal body weight, 0.2 µg./kg. animal body weight and 1 µg./kg. animal body weight respectively, the compounds produce falls of 18 mm.Hg, 20 mm.Hg and 18 mm.Hg respectively in blood-pressure. Trans-$\Delta^2$-PGE$_1$ also inhibits adenosine diphosphate induced blood platelet aggregation in platelet-rich plasma of rats and also in human blood, and with rat blood showed itself to have an activity 2.95 times that of PGE$_1$ and with human blood 7.15 times the activity of PGE$_1$.

As hereinbefore mentioned, the prostaglandin compounds of general formula XXXIV and, when R$^{3'}$ represents a hydrogen atom, non-toxic salts thereof, in particular trans-$\Delta^2$-PGE$_2$ methyl ester and, more especially, trans-$\Delta^2$-PGA$_2$ methyl ester, possess useful immuno-suppressive properties and are useful in the treatment of autoimmune conditions, for example rheumatoid arthritis, and other conditions believed to be of autoimmune origin e.g. psoriasis, lupus states of autoimmune origin, e.g. lupus erythematosus and acute systemic disseminated lupus, skin-graft and organ-transplant rejection, multiple sclerosis, Crohn's disease (regional ileitis) and ulcerative colitis, glomerulonephritis and nephrotic syndrome of autoimmune origin, i.e., not associated with bacterial infection, atherosclerosis and malignant paraproteinemias of autoimmune origin characterised by abnormal immunoglobulins and abnormal reticuloendothelial immune cells. For example, in laboratory screening tests indicative of immuno-suppressive properties:- (a) trans-$\Delta^2$-PGE$_2$ methyl ester and trans-$\Delta^2$-PGA$_2$ methyl ester produce in vitro inhibitions of blastformation of human lymphocytes stimulated by phytohemagglutinin of 65% and 99%, respectively, at a concentration of $10^{-5}$M and (b) trans-$\Delta^2$-PGA$_2$ methyl ester produces in vitro inhibition of deoxyribonucleic acid (DNA) synthesis by HeLa cells of 50% at a concentration of $3.6 \times 10^{-5}$M. When administered orally to mice rendered constipated by the administration of morphine, trans-$\Delta^2$-PGA$_2$ methyl ester produces no diarrhea at a dose of 100 µg./kg.

The following Reference Examples illustrate the preparation of starting materials of general formula employed in the process of the present invention. In all the Examples 'IR', 'MMR' and 'TLC' represent 'Infrared absorption spectrum', 'Nuclear magnetic resonance spectrum' and 'Thin layer chromatography' respectively.

REFERENCE EXAMPLE 1

Methyl-9α-hydroxy-11α,15α-bis-(2-tetrahydropyranyloxy)-prost-trans-13-enoate 1.31 g. (2.5 mmol) of 9α-hydroxy-11α,15α-bis-(2-tetrahydropyranyloxy)-prost-trans-13-enoic acid [prepared as described in J. Amer. Chem. Soc. 92, 2586 (1970)] were dissolved in 40 ml. of diethyl ether, and to the solution a freshly prepared ethereal solution of diazomethane was added so that the reaction mixture turned yellow. The reaction mixture was concentrated under reduced pressure at low temperature, and the residue purified by column chromatography on silica gel using ethyl acetatecyclohexane (2:5) as eluent to give 1.08 g. (80.3%) of the title compound having the following physical characteristics: IR (liquid film): 3450, 2930, 2850, 1738, 1438, 1130, 1020 and 980 cm$^{-1}$. MMR (deuterochloroform solution): δ= 5.60-5.25 (2H, m), 4.66 (2H, m), 3.60 (3H, s), 4.16-3.25 (7H, m). TLC (developing solvent; cyclohexane:ethyl acetate = 2:1): Rf = 0.36.

REFERENCE EXAMPLE 2

By the same procedure as described in Reference Example 1, the following compounds (a) to (m) were obtained from the corresponding acids of general formula a. methyl 9α-hydroxy-11α,15α-bis-(2-tetrahydropyranyloxy)-prosta-cis-5,trans-13-dienoate IR (liquid film): 3450, 2930, 2850, 1738, 1438, 1130, 1020, and 980 cm$^{-1}$.

MMR (deuterochloroform solution): δ= 5.62-5.20 (4H, m), 4.67 (2H, m), 3.64 (3H, s), 4.20–3.35 (7H, m).

TLC (developing solvent; cyclohexane:ethyl acetate = 2:1): Rf = 0.37.

b. methyl 9α-hydroxy-11α,15-bis-(2-tetrahydropyranyloxy)-15-methyl-prost-trans-13-enoate IR (liquid film): 3440, 2920, 2840, 1736, 1130, 1020 and 980 cm$^{-1}$.

NMR (deuterochloroform solution): δ= 5.53-5.26 (2H, m), 4.65 (2H, m), 3.63 (3H, s), 4.20-3.35 (6H, m).

TLC (developing solvent; cyclohexane:ethyl acetate = 2:1): Rf = 0.39.

c. methyl 9α-hydroxy-11α,15-bis-(2-tetrahydropyranyloxy)-15-methyl-prosta-cis-5,trans-13-dienoate IR (liquid film): 3440, 2930, 2840, 1737, 1130, 1020 and 980 cm$^{-1}$.

NMR (deuterochloroform solution): δ= 5.63–5.20 (4H, m), 4.66 (2H, m), 3.62 (3H, s), 4.20–3.35 (6H, m).

TLC (developing solvent; cyclohexane:ethyl acetate 2:1): Rf = 0.40.

d. methyl 9α-hydroxy-11α,15α-bis-(2-tetrahydropyranyloxy)16(R)-methyl-prost-trans-13-enoate IR (liquid film): 3440, 2930, 2840, 1737, 1130, 1020 and 980 cm$^{-1}$.

NMR (deuterochloroform solution): δ= 5.56-5.30 (2H, m), 4.67 (2H, m), 3.63 (3H, s), 4.20-3.30 (7H, m).

TLC (developing solvent; cyclohexane:ethyl acetate = 2:1): Rf = 0.36.

e. methyl 9α-hydroxy-11α,15α-bis-(2-tetrahydropyranyloxy)-16(R)-methyl-prosta-cis-5,trans-13-dienoate IR (liquid film): 3440, 2930, 2840, 1736, 1130, 1020 and 980 cm$^{-1}$.

NMR (deuterochloroform solution): δ= 5.65-5.25 (4H, m), 4.67 (2H, m), 3.64 (3H, s), 4.22-3.30 (7H, m).

TLC (developing solvent; cyclohexane:ethyl acetate = 2:1): Rf = 0.37.

f. methyl 9α-hydroxy-11α,15-bis-(2-tetrahydropyranyloxy)-17-methyl-prost-trans-13-enoate IR (liquid film): 3440, 2930, 2850, 1735, 1130, 1020 and 980 cm$^{-1}$.

NMR (deuterochloroform solution): δ= 5.55-5.30 (2H, m), 4.67 (2H, m), 3.64 (3H, s), 4.20-3.30 (7H, m).

TLC (developing solvent; cyclohexane:ethyl acetate = 2:1): Rf = 0.36.

g. methyl 9α-hydroxy-11α,15-bis-(2-tetrahydropyranyloxy)-17-methyl-prosta-cis-5,trans-13-dienoate IR (liquid film): 3440, 2920, 2840, 1736, 1130, 1020 and 980 cm$^{-1}$.

NMR (dueterochloroform solution): δ= 5.65-5.25 (4H, m), 4.67 (2H, m), 3.65 (3H, s), 4.22-3.25 (7H, m).

TLC (developing solvent; cyclohexane:ethyl acetate = 2:1): Rf = 0.37.

h. methyl 9α-hydroxy-11α,15-bis-(2-tetrahydropyranyloxy)15,16-dimethyl-prost-trans-13-enoate IR (liquid film): 3450, 2920, 2840, 1738, 1130, 1020 and 979 cm$^{-1}$.

NMR (deuterochloroform solution): δ= 5.65-5.30 (2H, m), 4.67 (2H, m), 3.64 (3H, s), 4.22-3.25 (6H, m).

TLC (developing solvent; cyclohexane:ethyl acetate 2:1): Rf = 0.39.

i. methyl 9α-hydroxy-11α,15-bis-(2-tetrahydropyranyloxy)-15,16-dimethyl-prosta-cis-5,trans-13-dienoate IR (liquid film): 3440, 2920, 2840, 1738, 1130, 1020 and 980 cm$^{-1}$.

NMR (deuterochloroform solution): δ= 5.72-5.28 (4H, m), 4.67 (2H, m), 3.65 (3H, s), 4.22-3.25 (6H, m).

TLC (developing solvent; cyclohexane:ethyl acetate = 2:1): Rf = 0.40.

j. methyl 9α-hydroxy-11α,15-bis-(2-tetrahydropyranyloxy)16-phenyl-ω-trinorprost-trans-13-enoate IR (liquid film): 3430, 3030, 2940, 1735, 1450, 1020 and 690 cm$^{-1}$.

NMR (deuterochloroform solution): δ= 7.10 (5H, m), 5.50-5.15 (2H, m), 4.58 (2H, m), 3.60 (3H, s), 4.10-3.20 (7H, m).

TLC (developing solvent; cyclohexane:ethyl acetate = 2:1): Rf = 0.38.

k. methyl 9α-hydroxy-11α,15-bis-(2-tetrahydropyranyloxy)16-phenyl-ω-trinorprosta-cis-5,trans-13-dienoate IR (liquid film): 3440, 3030, 2940, 1736, 1451, 1020 and 690 cm$^{-1}$.

NMR (deuterochloroform solution): δ= 7.10 (5H, m), 5.55-5.15 (4H, m), 4.60 (2H, m), 4.12-3.22 (7H, m).

TLC (developing solvent; cyclohexane:ethyl acetate = 2:1): Rf = 0.39.

l. methyl 9α-hydroxy-11α,15α-bis-(2-tetrahydropyranyloxy)16-cyclohexyl-ω-trinorprost-trans-13-enoate IR (liquid film): 3420, 2920, 2810, 1736, 1120, 1020 and 900 cm$^{-1}$.

NMR (deuterochloroform solution): δ= 5.50-5.20 (2H, m), 4.62 (2H, m), 3.55 (3H, s), 4.10-3.20 (7H, m).

TLC (developing solvent; cyclohexane:ethyl acetate = 2:1): Rf = 0.41.

m. methyl 9α-hydroxy-11α,15α-bis-(2-tetrahydropyranyloxy)-16-cyclohexyl-ω-trinorprosta-cis-5,trans-13-dienoate IR (liquid film): 3430, 2930, 2820, 1737, 1120, 1020 and 901 cm$^{-1}$.

NMR (deuterochloroform solution): δ= 5.60-5.20 (4H, m), 4.63 (2H, m), 3.57 (3H, s), 4.10-3.22 (7H, m).

TLC (developing solvent; cyclohexane:ethyl acetate = 2:1): Rf = 0.42.

The following Examples illustrate the process of the invention and products obtained thereby.

EXAMPLE 1

Methyl 9α-hydroxy-11α,15α-bis-(2-tetrahydropyranyloxy)-prostatrans-2,trans-13-dienoate 836 mg. of diphenyldiselenide were dissolved in 5 ml. of tetrahydrofuran, and to the solution 430 mg. of bromine were added dropwise at room temperature and the reaction mixture was stirred for 1 hour to obtain benzeneselenenyl bromide.

Separately, a solution of 470 mg. of diisopropylamine in 10 ml. of tetrahydrofuran was cooled to −70° C., and to it 3.61 ml. of a solution of n-butyllithium in hexane (1.3 molar concentration) were added dropwise and stirred for 15 minutes at −70° C. to give lithium diisopropylamide.

To the lithium diisopropylamide solution, 1.08 g. of methyl 9α-hydroxy-11α,15α-bis-(2-tetrahydropyranyloxy)prost-trans-13-enoate (prepared as described in Reference Example 1) in 5 ml. of tetrahydrofuran were added dropwise at −70° C. and the reaction mixture stirred for 30 minutes at the same temperature. The benzeneselenenyl bromide solution previously prepared was added dropwise to the reaction mixture at −70° C. and stirring was continued for 1 hour at the same temperature and then for 30 minutes at room temperature. The reaction mixture was poured into a small amount of a saturated aqueous solution of ammonium chloride, and extracted with 80 ml. of ethyl acetate. The organic layer was washed with a small amount of 1N hydrochloric acid and a saturated aqueous solution of sodium bicarbonate. Maintaining the temperature below 30° C., 1.4 ml. of 30% hydrogen peroxide were added dropwise and the reaction mixture stirred for 1 hour at 28° C. The reaction mixture was washed successively with water, a saturated aqueous solution of sodium carbonate and a saturated solution of sodium chloride, dried over anhydrous magnesium sulphate and concentrated under reduced pressure. The residue was purified by column chromatography on silica gel using cyclohexane-ethyl acetate (3:1) as eluent to give 643 mg. (60%) of the title compound having the following physical characteristics:

IR (liquid film): 3420, 2920, 2830, 1726, 1655, 1437, 1130, 1020 and 978 cm$^{-1}$.

NMR (deuterochloroform solution): $\delta=$ 6.86 (1H, dt), 5.72 (1H, dt), 5.56-5.23 (2H, m), 4.60 (2H, m), 3.65 (3H, s), 4.05-3.25 (7H, m).

TLC (developing solvent; cyclohexane:ethyl acetate = 2:1): Rf = 0.35.

EXAMPLE 2

Methyl 9α-hydroxy-11α,15α-bis-(2-tetrahydropyranyloxy)-prosta-trans-2,cis-5,trans-13-trienoate By the same procedure as described in Example 1, 641 mg. (60.0%) of the title compound were obtained from 1.07 g. of methyl 9α-hydroxy-11α,15α-bis-(2-tetrahydropyranyloxy)-prosta-cis-5,trans-13-dienoate [cf. Reference Example 2(a)], using diphenyldiselenide instead of benzeneselenenyl bromide as in Example 1. The title compound has the following physical characteristics:

IR (liquid film): 3430, 2920, 2830, 1722, 1655, 1435, 1275, 1130, 1020 and 978 cm$^{-1}$.

NMR (deuterochloroform solution): $\delta=$ 6.95 (1H, dt), 5.82 (1H, dt), 5.67-5.32 (4H, m), 4.66 (2H, m), 3.70 (3H, s), 4.16-3.32 (7H, m), 2.99 (2H, t).

TLC (developing solvent; cyclohexane:ethyl acetate = 2:1): Rf = 0.36.

EXAMPLE 3

Methyl 9α-hydroxy-11α,15-bis-(2-tetrahydropyranyloxy)-15-methyl-prosta-trans-2,trans-13-dienoate By the same procedure as described in Example 1, 666 mg. (60.5%) of the title compound were obtained from 1.10 g. of methyl 9α-hydroxy-11α,15-bis-(2-tetrahydropyranyloxy)-15-methyl-prost-trans-13-enoate [cf. Reference Example 2(b)]. The title compound has the following physical characteristics:

IR (liquid film): 3440, 2920, 2830, 1720, 1654, 1130 1020 and 975 cm$^{-1}$.

NMR (deuterochloroform solution): $\delta=$ 6.86 (1H, dt), 5.70 (1H, dt), 5.60-5.24 (2H, m), 4.61 (2H, m), 3.69 (3H, s), 4.10-3.55 (6H, m).

TLC (developing solvent; cyclohexane:ethyl acetate = 2:1): Rf = 0.38.

EXAMPLE 4

Methyl 9α-hydroxy-11α,15-bis-(2-tetrahydropyranyloxy)-15-methyl-prosta-trans-2,cis-5,trans-13-trienoate By the same procedure as described in Example 1, 647 mg. (59.0%) of the title compound were obtained from 1.10 g. of methyl 9α-hydroxy-11α,15-bis-(2-tetrahydropyranyloxy)-15-methyl-prosta-cis-5,trans-13-dienoate [cf. Reference Example 2(c)] using diphenyldiselenide instead of benzeneselenenyl bromide as in Example 1. The title compound has the following physical characteristics:

IR (liquid film): 3430, 2920, 2830, 1722, 1655, 1130, 1020 and 977 cm$^{-1}$.

NMR (deuterochloroform solution): $\delta=$ 6.95 (1H, dt), 5.80 (1H, dt), 5.67-5.35 (4H, m), 4.65 (2H, m), 3.70 (3H, s), 4.15-3.35 (6H, m), 3.00 (2H, t).

TLC (developing solvent; cyclohexane:ethyl acetate = 2:1): Rf = 0.39.

EXAMPLE 5

Methyl 9α-hydroxy-11α,15α-bis-(2-tetrahydropyranyloxy)-16(R)-methyl-prosta-trans-2,trans-13-dienoate By the same procedure as described in Example 1, 671 mg. (61.0%) of the title compound were obtained from 1.10 g. of methyl 9α-hydroxy-11α,15α-bis-(2-tetrahydropyranyloxy)-16(R)-methyl-prost-trans-13-enoate [cf. Reference Example 2(d)]. The title compound has the following physical characteristics:

IR (liquid film): 3410, 2930, 2850, 1722, 1650, 1130, 1020 and 972 cm$^{-1}$.

NMR (deuterochloroform solution): $\delta=$6.87 (1H, dt), 5.67 (1H, d), 5.31 (2H, m), 4.65 (2H, m), 3.71 (3H, s), 4.13-3.22 (7H, m).

TLC (developing solvent; cyclohexane:ethyl acetate = 2:1): Rf = 0.35.

EXAMPLE 6

Methyl 9α-hydroxy-11α,15α-bis-(2-tetrahydropyranyloxy)-16(R)-methyl-prosta-trans-2,cis-5,trans-13-trienoate By the same procedure as described in Example 1, 636 mg. (58.0%) of the title compound were obtained from 1.10 g. of methyl 9α-hydroxy-11α,15α-bis-(2-tetrahydropyranyloxy)-16(R)-methyl-prosta-cis-5,trans-13-dienoate [cf. Reference Example 2(e)] using diphenyldiselenide instead of benzeneselenenyl bromide as in Example 1. The title compound has the following physical characteristics:

IR (liquid film): 3420, 2920, 2830, 1723, 1650, 1130, 1020 and 977 cm$^{-1}$.

NMR (deuterochloroform solution): $\delta=$ 6.96 (1H, dt), 5.83 (1H, dt), 5.65-5.30 (4H, m), 4.65 (2H, m), 3.69 (3H, s), 4.16-3.35 (7H, m), 3.00 (2H, t).

TLC (developing solvent; cyclohexane:ethyl acetate = 2:1): Rf = 0.36.

EXAMPLE 7

Methyl 9α-hydroxy-11α,15-bis-(2-tetrahydropyranyloxy)-17-methyl-prosta-trans-2,-trans-13-dienoate By the same procedure as described in Example 1, 652 mg. (59.3%) of the title compound were obtained from 1.10 g. of methyl-9α-hydroxy-11α,15-bis-(2-tetrahydropyranyloxy)-17-methyl-prost-trans-13-enoate [cf. Reference Example 2(f)]. The title compound has the following physical characteristics:

IR (liquid film): 3420, 2920, 2820, 1725, 1650, 1130, 1020 and 974 cm$^{-1}$.

NMR (deuterochlorofuran solution): $\delta=$6.87 (1H, dt), 5.66 (1H, dt), 5.50-5.25 (2H, m), 4.60 (2H, m), 4.60 (2H, m), 3.70 (3H, s), 4.12-3.25 (7H, m).

TLC (developing solvent; cyclohexane:ethyl acetate = 2:1): Rf = 0.35.

EXAMPLE 8

Methyl 9α-hydroxy-11α,15-bis-(2-tetrahydropyranyloxy)-17-methyl-prosta-trans-2,cis-5,-trans-13-trienoate By the same procedure as described in Example 1, 648 mg. (59.1%) of the title compound were obtained from 1.10 g. of methyl 9α-hydroxy-11α,15-bis-(2-tetrahydropyranyloxy(-17-methyl-prosta-cis-5,-trans-13-dienoate [cf. Reference Example 2(g)] using diphenyldiselenide in the place of benzeneselenenyl bromide as in Example 1. The title compound has the following physical characteristics:

IR (liquid film): 3420, 2920, 2820, 1725, 1650, 1130, 1020 and 977 cm$^{-1}$.

NMR (deuterochloroform solution): δ= 6.95 (1H, dt), 6.83 (1H, dt), 5.67-5.33 (4H, m), 4.65 (2H, m), 3.70 (3H, s), 4.16-3.32 (7H, m), 2.98 (2H, t).

TLC (developing solvent; cyclohexane:ethyl acetate = 2:1): Rf = 0.36.

EXAMPLE 9

Methyl-9α-hydroxy-11α,15-bis-(2-tetrahydropyranyloxy)-15,16-dimethyl-prosta-trans-2,-trans-13-dienoate By the same procedure as described in Example 1, 649 mg. (57.5%) of the title compound were obtained from 1.13 g. of methyl 9α-hydroxy-11α,15α-bis-(2-tetrahydropyranyloxy)-15,16-dimethyl-prost-trans-13-enoate [cf. Reference Example 2(h)]. The title compound has the following physical characteristics:

IR (liquid film): 3450, 2920, 2830, 1720, 1650, 1120, 1020 and 979 cm$^{-1}$.

NMR (deuterochloroform solution): δ=6.87 (1H, dt), 5.68 (1H, d), 5.70-5.30 (2H, m), 4.64 (2H, m), 3.69 (3H, s), 4.15-3.27 (6H, m).

TLC (developing solvent; cyclohexane:ethyl acetate = 2:1): Rf = 0.38.

EXAMPLE 10

Methyl 9α-hydroxy-11α,15-bis-(2-tetrahydropyranyloxy)-15,16-dimethyl-prosta-trans-2,-cis-5,-trans-13-trienoate By the same procedure as described in Example 1, 638 mg. (56.8%) of the title compound were obtained from 1.13 g. of methyl 9α-hydroxy-11α,15-bis-(2-tetrahydropyranyloxy)-15,16-dimethyl-prosta-cis-5,-trans-13-dienoate [cf. Reference Example 2(i)]using diphenyldiselenide instead of benzeneselenenyl bromide as in Example 1. The title compound has the following physical characteristics:

IR (liquid film): 3430, 2920, 2830, 1720, 1652, 1130, 1020 and 978 cm$^{-1}$.

NMR (deuterochloroform solution): δ=6.96 (1H, dt), 5.81 (1H, dt), 5.67-5.35 (4H, m), 4.65 (2H, m), 3.70 (3H, s), 4.15-3.36 (6H, m), 3.01 (2H, t).

TLC (developing solvent; cyclohexane:ethyl acetate = 2:1): RF = 0.39.

EXAMPLE 11

Methyl 9α-hydroxy-11α,15-bis-(2-tetrahydropyranyloxy)-16-phenyl-ω-trinorprost-trans-2,-trans-13-dienoate By the same procedure as described in Example 1, 661 mg. (58.0%) of the title compound were obtained from 1.14 g. of methyl 9α-hydroxy-11α,15-bis-(2-tetrahydropyranyloxy)-16-phenyl-ω-trinorprost-trans-13-enoate [cf. Reference Example 2(j)]. The title compound has the following physical characteristics:

IR (liquid film): 3450, 3030, 2940, 1720, 1650, 1023 and 690 cm$^{-1}$.

NMR (deuterochloroform solution): δ= 7.12 (5H, m), 6.87 (1H, dt), 5.69 (1H, d), 5.50-5.20 (2H, m), 4.61 (2H, m), 3.72 (3H, s), 4.10-3.20 (7H, m).

TLC (developing solvent; cyclohexane:ethyl acetate = 2:1): RF = 0.37.

EXAMPLE 12

Methyl 9α-hydroxy-11α,15-bis-(2-tetrahydropyranyloxy)-16-phenyl-ω-trinorprosta-trans-2,-cis-5,-trans-13-trienoate By the same procedure as described in Example 1, 648 mg. (57.0%) of the title compound were obtained from 1.14 g. of methyl 9α-hydroxy-11α,15-bis-(2-tetrahydropyranyloxy)-16-phenyl-ω-trinorprosta-cis-5,-trans-13-dienoate [cf. Reference Example 2(k)] using diphenyl diselenide instead of benzeneselenenyl bromide as in Example 1. The title compound has the following physical characteristics:

IR (liquid film): 3440. 3030, 2940, 1720, 1650, 1023 and 692 cm$^{-1}$.

NMR (deuterochloroform solution): δ= 7.13 (5H, m), 6.88 (1H, dt), 5.70 (1H, dt), 5.68-5.35 (4H, m), 4.62 (2H, m), 3.71 (3H, s), 4.16-3.35 (7H, m), 3.01 (2H, m).

TLC (developing solvent; cyclohexane:ethyl acetate = 2:1): Rf = 0.38.

EXAMPLE 13

Methyl 9α-hydroxy-11α,15α-bis-(2-tetrahydropyranyloxy)-16-cyclohexyl-ω-trinorprosta-trans-2,-trans-13-dienoate By the same procedure as described in Example 1, 674 mg. (58.5%) of the title compound were obtained from 1.16 g. of methyl 9α-hydroxy-11α,15α-bis-(2-tetrahydropyranyloxy)-16-cyclohexyl-ω-trinorprost-trans-13-enoate [cf. Reference Example 2(1)]. The title compound has the following physical characteristics:

IR (liquid film): 3440, 2900, 2820, 1720, 1651, 1120, 1020 and 901 cm$^{-1}$.

NMR (deuterochloroform solution): δ= 6.84 (1H, dt), 5.65 (1H, d), 5.50-5.20 (2H, m), 4.61 (2H, m), 3.68 (3H, s), 4.10-3.20 (7H, m).

TLC (developing solvent; cyclohexane:ethyl acetate = 2:1): RF = 0.40.

EXAMPLE 14

Methyl 9α-hydroxy-11α,15α-bis-(2-tetrahydropyranyloxy)-16-cyclohexyl-ω-trinorprosta-trans-2,cis-5,-trans-13-trienoate By the same procedure as described in Example 1, 669 mg. (58.3%) of the title compound were obtained from 1.15 g. of methyl 9α-hydroxy-11α,15α-bis-(2-tetrahydropyranyloxy)-16-cyclohexyl-ω-trinorprosta-cis-5,-trans-13-dienoate [cf. Reference Example 2(m)]using diphenyldiselenide instead of benzeneselenenyl bromide as in Example 1. The title compound has the following physical characteristics:

IR (liquid film): 3440, 2920, 2820, 1720, 1650, 1120, 1020 and 901 cm$^{-1}$. NMR (deuterochloroform solution): δ= 6.95 (1H, dt), 5.82 (1H, dt), 5.67-5.35 (4H, m), 4.66 (2H, m), 3.70 (3H, s), 4.16-3.31 (7H, m), 2.98 (2H, t).

TLC (developing solvent; cyclohexane:ethyl acetate = 2:1): Rf = 0.42.

By procedures described in the specification of United States Patent Application 427,403, the products of Examples 1, 5 and 7 were converted to trans-$\Delta^2$-PGF$_{1\alpha}$, -trans-$\Delta^2$-PGE$_1$, trans-$\Delta^2$-PGA$_1$, 16(R)-methyl-trans-$\Delta^2$-PGF$_{1\alpha}$, 17-methyltrans-$\Delta^2$-PGF$_{1\alpha}$ and 17-methyl-trans-$\Delta^2$-PGE$_1$. Also the products of Examples 3, 9, 11 and 13 were converted using procedures described in the aforesaid application to 15-methyl-trans-$\Delta^2$-PGF$_{1\alpha}$, 15-methyl-trans-$\Delta^2$-PGE$_1$, 15-methyl-trans-$\Delta^2$-PGA$_1$, 15,16-dimethyl-trans-$\Delta^2$-PGF$_{1\alpha}$, 15,16-dimethyl-trans-$\Delta^2$-PGE$_1$, 15,16-dimethyl-trans-$\Delta^2$-PGA$_1$, 16-phenyl-ω-trinor-trans-$\Delta^2$-PGF$_{1\alpha}$, 16-phenyl-ω-trinor-trans-$\Delta^2$-PGE$_1$, 16-phenyl-ω-trinor-trans-$\Delta^2$-PGA$_1$, 16-cyclohexyl-ω-trinor-trans-$\Delta^2$-PGF$_{1\alpha}$, 16-cyclohexyl-ω-trinor-trans-$\Delta^2$-PGE$_1$ and 16-cyclohexyl-ω-trinor-trans-$\Delta^2$-PGA$_1$.

Furthermore, the products of Examples 2, 4, 6, 8, 10, 12 and 14 were converted to the corresponding novel trans-$\Delta^2$-prostaglandin analogues as described in the following Examples 15 to 20.

EXAMPLE 15

Trans-$\Delta^2$-PGF$_{2\alpha}$ methyl ester 260 mg. of methy 9α-hydroxy-11α,15α-bis-(2-tetrahydropyranyloxy)-prosta-trans-2,cis-5,trans-13-trienoate (prepared as described in Example 2) were dissolved in 40 ml. of a mixture of 1N hydrochloric acid and tetrahydrofuran (1:1), and the solution stirred for 1 hour at room temperature, then poured into 100 ml. of ice-water and extracted with ethyl acetate. The combined extracts were washed with water, dried and concentrated under reduced pressure. The residue was purified by column chromatography on silica gel using ethyl acetate-cyclohexane (2:1) as eluent to give 138 mg. of the title compound having the following physical characteristics:

IR (liquid film): 3350, 2920, 2840, 1720, 1650, 1430, 1280, 1170 and 973 cm$^{-1}$.

NMR (deuterochloroform solution): δ= 6.95 (1H, dt), 5.82 (1H, dt), 5.65-5.26 (4H, m), 4.16-3.65 (3H, m), 3.71 (3H, s), 2.98 (2H, t), 0.88 (3H, t).

TLC (developing solvent; chloroform:tetrahydrofuran:acetic acid = 10:2:1): Rf = 0.13.

EXAMPLE 16

By the same procedure as described in Example 15, the following compounds (a) to (f) were obtained from the title products synthesized in Examples 4, 6, 8, 10, 12 and 14 respectively.

a. 15-methyl-trans-$\Delta^2$-PGF$_{2\alpha}$ methyl ester.

IR (liquid film): 3360, 2920, 2840, 1720, 1650, 1170 975 cm$^{-1}$.

NMR (deuterochloroform solution): δ=6.95 (1H, dt), 5.82 (1H, dt), 5.64-5.30 (4H, m), 4.21-3.90 (2H, m), 3.70 (3H, s), 2.97 (2H, t), 0.88 (3H, t).

TLC (developing solvent; chloroform:tetrahydrofuran:acetic acid = 10:2:1): RF = 0.16.

b. 16(R)-methyl-trans-$\Delta^2$-PGF$_{2\alpha}$ methyl ester.

IR (liquid film); 3350, 2920, 2840, 1720, 1650, 1280, 1170 and 975 cm$^{-1}$.

NMR (deuterochloroform solution): δ= 6.95 (1H, dt), 5.83 (1H, dt), 5.62-5.33 (4H, m), 4.24-3.83 (3H, m), 3.72 (3H, s), 2.97 (2H, t).

TLC (developing solvent; chloroform:tetrahydrofuran:acetic acid = 10:2:1): Rf = 0.15.

c. 17-methyl-trans-$\Delta^2$-PGF$_{2\alpha}$ -methyl ester.

IR (liquid film): 3360, 2920, 2840, 1720, 1652, 1280, 1170 and 976 cm$^{-1}$.

NMR (deuterochloroform solution): δ= 6.96 (1H, dt), 5.83 (1H, dt), 5.63-5.55 (4H, m), 4.26-3.83 (3H, m), 3.72 (3H, s), 2.98 (2H, t).

TLC (developing solvent; chloroform:tetrahydrofuran:acetic acid = 10:2:1): Rf = 0.14.

d. 15,16-dimethyl trans-$\Delta^2$-PGF$_{2\alpha}$ methyl ester.

IR (liquid film): 3360, 2920, 1720, 1650, 1280, 1175 and 975 cm$^{-1}$.

NMR (deuterochloroform solution): δ= 6.95 (1H, dt), 5.83 (1H, dt), 5.63-5.28 (4H, m), 4.25-3.90 (2H, m), 3.72 (3H, s), 2.98 (2H, t).

TLC (developing solvent; chloroform:tetrahydrofuran:acetic acid = 10:2:1): Rf = 0.16.

e. 16-phenyl-ω-trinor-trans-$\Delta^2$-PGF$_{2\alpha}$ methyl ester.

IR (liquid film): 3340, 2920, 2840, 1720, 1650, 980 and 680 cm$^{-1}$.

NMR (deuterochloroform solution): δ= 7.25 (5H, m), 7.00 (1H, dt), 5.85 (1H, dt), 5.62-5.35 (4H, m), 4.20-3.80 (3H, m), 3.71 (3H, s), 2.98 (2H, t), 2.75 (1H, m), 1.21 (3H, d).

TLC (developing solvent; chloroform:tetrahydrofuran:acetic acid = 10:2:1): Rf = 0.17.

f. 16-cyclohexyl-ω-trinor-trans-$\Delta^2$-PGF$_{2\alpha}$ methyl ester.

IR (liquid film): 3350, 2920, 2840, 1722, 1650, 1290, 1180 and 975 cm$^{-1}$.

NMR (deuterochloroform solution): δ=6.96 (1H, dt), 5.83 (1H, dt), 5.60-5.32 (4H, m), 4.20-3.70 (3H, m), 3.70 (3H, s), 2.98 (2H, t), 0.78 (3H, d).

TLC (developing solvent; chloroform:tetrahydrofuran:acetic acid = 10:2:1): Rf = 0.16.

EXAMPLE 17

Trans-$\Delta^2$-PGE$_2$methyl ester 260 mg. of methyl 9α-hydroxy-11α,15α-bis-(2-tetrahydropyranyloxy)-prosta-trans-2,-cis-5,-trans-13-trienoate (prepared as described in Example 2) were dissolved in 10 ml. of diethyl ether and cooled with an ice-bath. To the cooled solution, a solution of 1.7 g. of manganese sulphate, 0.34 g. of chromium trioxide and 0.38 ml. of conc. sulphuric acid in 8 ml. of water was added, and the mixture stirred for 2 hours at 0°to 5° C. 200 ml. of dimethyl ether were added to the solution and, after separation, the aqueous layer was saturated with sodium sulphate and extracted with diethyl ether. The combined ethereal extracts were washed with water, dried and concentrated. The residue was purified by column chromatography on silica gel using ethyl acetate-benzene (1:6) as eluent to give methyl 9-oxo-11α,15α-bis-(2-tetrahydropyranyloxy)prosta-trans-2,:cis-5,-trans-13-trienoate.

The bis-tetrahydropyranyl ether was dissolved in a mixture of 4 ml. of acetic acid, 2.4 ml. of water and 0.5 ml. of tetrahydrofuran, and the solution stirred for 2 hors at 40° C. 20 ml. of ice-water were added and the mixture then extracted with ethyl acetate. The extracts were washed with water, dried and concentrated under reduced pressure. The residue was purified by column chromatography on silica gel using cyclohexane-ethyl acetate (1:2) as eluent to give 80 mg. of the title compound having the following physical characteristics:

IR (liquid film): 3370, 2920, 2840, 1738, 1717, 1647, 1275, 1160 and 970 cm$^{-1}$.

NMR (deuterochloroform solution): δ= 6.92 (1H, dt), 5.81 (1H, dt), 5.64-5.30 (4H, m), 4.15-3.90 (2H, m), 3.72 (3H, s), 3.02-2.60 (3H, m), 0.90 (3H, t).

TLC (developing solvent; chloroform:tetrahydrofuran-acetic acid = 10:2:1): Rf = 0.29.

EXAMPLE 18

By the same procedure as described in Example 17, the following compounds (a) to (f) were obtained from the title products synthesized in Examples 4, 6, 8, 10, 12 and 14 respectively.

a. 15-methyl-trans-$\Delta^2$-PGE$_2$ methyl ester.

IR (liquid film): 3360, 2920, 2840, 1739, 1716, 1650, 1280, 1165 and 970 cm$^{-1}$.

NMR (deuterochloroform solution): δ= 6.92 (1H, dt), 5.90-5.35 (5H, m), 4.05 (1H, m), 3.72 (3H, s), 3.02-2.62 (3H, m), 0.90 (3H, t).

TLC (developing solvent; chloroform:tetrahydrofuran:acetic acid = 10:2:1): Rf = 0.32.

b. 16(R)-methyl-trans-$\Delta^2$-PGE$_2$ methyl ester.

IR (liquid film): 3370, 2920, 2840, 1737, 1715, 1648, 1270, 1160 and 970 cm$^{-1}$.

NMR (deuterochloroform solution): δ= 6.92 81H, dt), 5.82 (1H, dt), 5.62-5.33 (4H, m), 4.12-3.90 (2H, m), 3.72 (3H, s), 3.03-2.60 (3H, m).

TLC (developing solvent; chloroform:tetrahydrofuran:acetic acid =10:2:1): Rf = 0.31.

c. 17-methyl-trans-$\Delta^2$-PGE$_2$ methyl ester.

IR (liquid film): 3370, 2920, 2840, 1735, 1716, 1649, 1270, 1160 and 972 cm$^{-1}$.

NMR (deuterochloroform solution): δ= 6.92 (1H, dt), 5.81 (1H, dt), 5.64-5.33 (4H, m), 4.30-3.94 (2H, m), 3.72 (3H, s), 3.30-2.60 (3H, m).

TLC (devoloping solvent; chloroform:tetrahydrofuran:acetic acid = 10:2:1): Rf = 0.30.

d. 15,16-dimethyl-trans-$\Delta^2$-PGE$_2$ methyl ester. IR (liquid film): 3360, 2920, 2840, 1738, 1719, 1650, 1276, 1162 and 973 cm$^{-1}$.

NMR (deuterochloroform solution): δ= 6.93 (1H, dt), 5.89-5.34 (5H, m), 4.24-3.95 (1H, m), 3.72 (3H, s), 3.03-2.62 (3H, m).

TLC (developing solvent; chloroform:tetrahydrofuran:acetic acid = 10:2:1): Rf = 0.32.

e. 16-phenyl-ω-trinor-trans-$\Delta^2$-PGE$_2$ methyl ester. IR (liquid film): 3360, 2920, 2840, 1738, 1718, 1650, 980 and 685 cm$^{-1}$.

NMR (deuterochloroform solution): δ= 7.26 (5H, m), 7.01 (1H, dt), 5.83 (1H, dt), 5.57-5.33 (4H, m), 4.10-3.80 (2H, m), 3.72 (3H, s), 1.15 (3H, d).

TLC (developing solvent; chloroform:tetrahydrofuran:acetic acid = 10:2:1): Rf = 0.33.

f. 16-cyclohexyl-107 -trinor-trans-$\Delta^2$-PGE$_2$ methyl ester. IR (liquid film): 3370, 2920, 2840, 1738, 1718, 1649, 1272, 1160 and 970 cm$^{-1}$.

NMR (deuterochloroform solution): δ= 6.92 (1H, dt), 5.81 (1H, dt), 5.62-5.35 (4H, m), 4.20-3.92 (2H, m), 3.72 (3H, s), 3.02-2.64 (3H, m), 0.78 (3H, d). TLC developing solvent; chloroform:tetrahydrofuran:acetic acid = 10:2:1): Rf = 0.32.

EXAMPLE 19

TRANS-$\Delta^2$-PGA$_2$ methyl ester 178 mg. of trans-$\Delta^2$-PGE$_2$ methyl ester (prepared as described in Example 17) were dissolved in 15 ml. of 90% acetic acid and the solution stirred for 17 hours at 57° to 60° C. The reaction mixture was then concentrated under reduced pressure. The residue was dissolved in diethyl ether, washed with water, dried and concentrated under reduced pressure. The residue was purified by column chromatography on silica gel using cyclohexaneethyl acetate (4:1) as eluent to give 106 mg. of the title compound having the following physical characteristics:

IR (liquid film): 3430, 2920, 2850, 1718, 1650, 1590, 1430, 1280, 1170 and 970 cm$^{-1}$.

NMR (deuterochloroform solution): δ= 7.50 (1H, dd), 6.95 (1H, dt), 6.19 (1H, dd), 5.83 (1H, dt), 5.64-5.46 (4H, m), 4.10 (1H, m), 3.72 (3H, s), 3.22 (1H, m), 2.98 (2H, t), 0.89 (3H, t).

TLC (devoloping solvent; chloroform:tetrahydrofuran:acetic acid = 10:2:1): Rf = 0.72.

EXAMPLE 20

By the same procedure as described in Example 19, the following compounds (a) to (f) were obtained from the corresponding products synthesized in Example 18 (a) to (f) respectively.

a. 15-methyl-trans-$\Delta^2$-PGA$_2$ methyl ester. IR (liquid film): 3340, 2920, 2850, 1719, 1650, 1590, 1280, 1160 and 970 cm$^{-1}$.

NMR (deuterochloroform solution): δ= 7.50 (1H, dd), 6.96 (1H, dt), 6.19 (1H, dd), 5.89-5.48 (5H, m), 3.72 (3H, s), 3.22 (1H, m), 2.98 (2H, t), 0.89 (3H, t).

TLC (developing solvent; chloroform:tetrahydrofuran:acetic acid = 10:2:1): Rf = 0.75.

b. 16(R)-methyl-trans-$\Delta^2$-PGA$_2$ methyl ester. IR (liquid film): 3430, 2920, 2850, 1718, 1650, 1590, 1280, 1170 and 970 cm$^{-1}$.

NMR (deuterochloroform solution): δ= 7.50 (1H, dd), 6.95 (1H, dt), 6.18 (1H, dd), 5.82 (1H, dt), 5.64-5.45 (4H, m), 4.22 (1H, m), 3.72 (3H, s), 3.24 (1H, m), 2.98 (2H, t).

TLC (developing solvent; chloroform:tetrahydrofuran:acetic acid = 10:2:1): Rf = 0.74.

c. 17-methyl-trans-$\Delta^2$-PGA$_2$ methyl ester.

IR (liquid film): 3430, 2920, 2850, 1718, 1650, 1590, 1170 and 970 cm$^{-1}$.

NMR (deuterochloroform solution): δ= 7.51 (1H, dd), 6.96 (1H, dt), 6.18 (1H, dd), 5.82 (1H, dt), 5.65-5.37 (4H, m), 4.23 (1H, m), 3.72 (3H, s), 3.24 (1H, m), 2.98 (2H, m).

TLC (developing solvent; chloroform:tetrahydrofuran:acetic acid = 10:2:1): Rf = 0.73.

d. 15,16-dimethyl-trans-$\Delta 2$-PGA$_2$ methyl ester.

IR (liquid film): 3440, 2920, 2850, 1718, 1650, 1590, 1280, 1162 and 973 cm$^{-1}$.

NMR (deuterochloroform solution): δ= 7.50 (1H, dd), 6.96 (1H, dt), 6.17 (1H, dd), 5.90-5.40 (5H, m), 3.72 (3H, s), 3.21 (1H, m), 2.99 (2H, t).

TLC (devoloping solvent; chloroform-tetrahydrofuran:acetic acid = 10:2:2): Rf = 0.75.

e. 16-phenyl-ω-trinor-trans-$\Delta^2$-PGA$_2$ methyl ester.

IR (liquid film): 3430, 3030, 2920, 2850, 1718, 1650, 1590, 970 and 670 cm$^{-1}$.

NMR (deuterochloroform solution): δ= 7.45 (1H, dd), 7.28 (5H, m), 6.95 (1H, dt), 6.20 (1H, dd), 5.85 (1H, dt), 5.65-5.35 (4H, m), 4.18 (1H, m), 3.72 (3H, s), 3.26 (1H, m), 3.05-2.75 (3H, m), 1.25 (3H, d).

TLC (developing solvent; chloroform:tetrahydrofuran:acetic acid = 10:2:1): Rf = 0.76.

f. 16-cyclohexyl-ω-trinor-trans-$\Delta^2$-PGA$_2$ methyl ester.

IR (liquid film): 3430, 2920, 2850, 1718, 1650, 1590, 1280, 1170 and 970 cm$^{-1}$.

NMR (deuterochloroform solution): δ= 7.52 (1H, dd), 6.95 (1H, dt), 6.22 (1H, dd), 5.85 (1H, dt), 5.62-5.40 (4H, m), 4.10 (1H, m), 3.72 (3H, s), 3.28 (1H, m), 2.98 (2H, t), 0.78 (3H, d).

TLC (developing solvent; chloroform:tetrahydrofuran:acetic acid = 10:2:1): Rf = 0.75.

EXAMPLE 21

Methyl 9α-hydroxy-11α,15α-bis-(2-tetrahydropyranyloxy)-prosta-trans-2,trans-13-dienoate 242 mg. of diisopropylamine in 7 ml. of tetrahydrofuran were cooled to −70° C. 240 ml. of a solution of n-butyllithium in n-hexane (one molar concentration) were added dropwise, and the mixture stirred for 15 minutes at −70° C. to form lithium diisopropylamide. To the reaction mixture, 537 mg. of methyl 9α-hydroxy-11α,15α-bis-(2-tetrahydropyranyloxy-prost-trans-13-enoate (prepared as described in Reference Example 1) in 6 ml. of tetrahydrofuran were added dropwise slowly, and the mixture at the same temperature stirred for 30 minutes. Maintaining the temperature at −70° C., the reaction mixture was added dropwise slowly to a cooled solution of 260 mg. of dimethyldisulphide in 2 ml. of tetrahydrofuran and stirred for 30 minutes at the same temperature and for a further 30 minutes at 15° C. The reaction mixture was then poured into a small amount of a saturated aqueous solution of ammonium chloride, and extracted three times with ethyl acetate. The organic extracts were washed with 1N hydrochloric acid and a saturated aqueous sodium chloride solution, dried over magnesium sulphate and concentrated under reduced pressure. The residue was purified by column chromatography on silica gel using cyclohexane-ethyl acetate (3:1) as eluent to give 356 mg. of pure methyl 2-methylthio-9α-hydroxy-11α,15α-bis-(2-tetrahydropyranyloxy)-prost-trans-13-enoate having the following physical characteristics:

IR (liquid film): 3440, 2920, 2850, 1730, 1435, 1155, 1130, 1020 and 977 cm$^{-1}$.

NMR (deuterochloroform solution): δ= 5.60-5.30 (2H, m), 4.67 (2H, m), 4.20-3.30 (7H, m), 3.73 (3H, s), 3.16 (1H, dd), 2.12 (3H, s).

TLC (developing solvent; cyclohexane:ethyl acetate = 2:1): Rf = 0.38.

To a solution of 292 mg. of the obtained thioether in 20 ml. of methanol, a solution of 321 mg. of sodium periodate in 3 ml. of water was added and the mixture stirred at 20° C. for 24 hours. Precipitated colourless solid was filtered off, and the filtrate concentrated under reduced pressure. The residue was dissolved in chloroform, washed with water and a saturated aqueous sodium chloride solution, dried over magnesium sulphate and concentrated under reduced pressure. The residue was purified by column chromatography on silica gel using benzene-ethanol (95:5) as eluent to give 246 mg. of pure methyl 2-methylsulphoxy-9α-hydroxy-11α,15α-bis-(2-tetrahydropyranyloxy)-prost-trans-13-enoate having the following physical characteristics:

IR (liquid film): 3420, 2920, 2830, 1732, 1438, 1200, 1130, 1020 and 977 cm$^{-1}$.

NMR (deuterochloroform solution): δ= 5.66-5.30 (2H, m), 4.66 (2H, m), 3.79 (3H, d), 4.20-3.30 (8H, m), 2.61 (3H, d).

TLC (developing solvent; benzene:ethanol =90:10): Rf = 0.44.

100 mg. of calcium carbonate were added to a solution of 100 mg. of the obtained sulphoxide in 10 ml. of toluene, the mixture stirred at 110° C. for 24 hours and afterwards the calcium carbonate filtered off. The filtrate was concentrated under reduced pressure, and the residue purified by column chromatography on silica gel using cyclohexane-ethyl acetate (3:1) as eluent to give 70 mg. of the title compound having the following physical characteristics:

IR (liquid film): 3430, 2920, 2840, 1725, 1655, 1440, 1200, 1130, 1020 and 980 cm$^{-1}$.

NMR (tetrachloromethane solution): δ= 6.88 (1H, dt), 5.70 (1H, dt), 5.50-5.24 (2H, m), 4.60 (2H, m), 3.65 (3H, s), 4.07-3.30 (7H, m).

TLC (developing solvent; cyclohexane:ethyl acetate = 2:1): Rf = 0.35.

EXAMPLE 22

Methyl 9α-hydroxy-11α,15α-bis-(2-tetrahydropyranyloxy)-prosta-trans-2,cis-5,trans-13-trienoate 242 mg. of diisopropylamine in 7 ml. of tetrahydrofuran were cooled to −70° C. 240 ml. of a solution of n-butyllithium in n-hexane (one molar concentration) were added dropwise, and the mixture stirred for 15 minutes at −70° C. to form lithium diisopropylamide. To the reaction mixture, 536 mg. of methyl 9α-hydroxy-11α,15α-bis-(2-tetrahydropyranyloxy)prosta-cis-5,trans-13-dienoate [cf. Reference Example 2(a)] in 6 ml. of tetrahydrofuran were added dropwise slowly and the mixture at the same temperature stirred for 30 minutes. Maintaining the temperature at −70° C., the reaction mixture was added dropwise slowly to a cooled solution of 260 mg. of dimethyldisulphide in 2 ml. of tetrahydrofuran, and stirred for 30 minutes at the same temperature and for a further 30 minutes at 15° C. The reaction mixture was then poured into a small amount of a saturated aqueous solution of ammonium chloride, and extracted three times with ethyl acetate. The organic extracts were washed with 1N hydrochloric acid and a saturated aqueous sodium chloride solution, dried over magnesium sulphate and concentrated under reduced pressure. The residue was dissolved in 25 ml. of methanol, and a solution of 392 mg. of sodium periodate in 4 ml. of water was added and the mixture stirred at 20° C. for 24 hours. Precipitated colourless solid was filtered off, and the filtrate concentrated under reduced pressure. The residue was dissolved in chloroform, washed with water and a saturated aqueous sodium chloride solution, dried over magnesium sulphate and concentrated under reduced pressure.

246 ml. of calcium carbonate were added to the residue dissolved in 25 ml. of toluene, and, after stirring the mixture at 110° C. for 24 hours, the calcium carbonate was filtered off. The filtrate was concentrated under reduced pressure, and the residue purified by column chromatography on silica gel using cyclohexane-ethyl acetate (3:1) as eluent to give 172 mg. of the title compound having the following physical characteristics:

IR (liquid film): 3430, 2920, 2830, 1722, 1655, 1435, 1275, 1130, 1020 and 978 cm⁻¹.

NMR (deuterochloroform solution): δ= 6.95 (1H, dt), 5.82 (1H, dt), 5.67-5.32 (4H, m), 4.66 (2H, m), 3.70 (3H, s), 4.16-3.32 (7H, m), 2.99 (2H, t).

TLC (developing solvent; cyclohexane:ethyl acetate = 2:1): Rf = 0.36.

EXAMPLE 23

Methyl 9α-hydroxy-11α,15-bis-(2-tetrahydropyranloyx)-15-methylprosta-trans-2,trans-13-dienoate By the same procedure as described in Example 22, 177 mg. of the title compound were obtained from 552 mg. of methyl 9α-hydroxy-11α,15-bis-(2-tetrahydropyranyloxy)-15-methylprost-trans-13-enoate [cf. Reference Example 2(b)].

IR (liquid film): 3440, 2920, 2830, 1720, 1654, 1130, 1020 and 975 cm⁻¹.

NMR (deuterochloroform solution): δ= 6.86 (1H, dt), 5.70 (1H, d), 5.60-5.24 (2H, m), 4.61 (2H, m), 3.69 (3H, s), 4.10-3.35 (6H, m).

TLC (developing solvent; cyclohexane:ethyl acetate = 1:1): Rf = 0.38.

EXAMPLE 24

Methyl 9α-hydroxy-11α,15-bis-(2-tetrahydropyranyloxy)-15-methylprosta-trans-2,cis-5,-trans-13-trienoate By the same procedure as described in Example 22, 170 mg. of the title compound were obtained from 550 mg. of methyl 9α-hydroxy-11α,15-bis-(2-tetrahydropyranyloxy)-15-methylprosta-cis-5,trans-13-dienoate [cf. Reference Example 2 (c)].

IR (liquid film): 3430, 2920, 1722, 1655, 1130, 1020 and 977 cm⁻¹.

NMR (deuterochloroform solution): δ= 6.95 (1H, dt), 5.80 (1H, dt), 5.67-5.35 (4H, m), 4.65 (2H, m), 3.70 (3H, s), 4.15-3.35 (6H, m), 3.00 (2H, t).

TLC (developing solvent; cyclohexane:ethyl acetate = 2:1): Rf = 0.39.

EXAMPLE 25

Methyl 9α-hydroxy-11α,15α-bis-(2-tetrahydropyranyloxy)-16(R)-methylprosta-trans-2,trans-13-dienoate BY the same procedure as described in Example 22, 180 mg. of the title compound were obtained from 552 mg. of methyl 9α-hydroxy-11α,15α-bis-(2-tetrahydropyranyloxy)-16(R)-methylprost-trans-13-enoate [cf. Reference Example 2(d)].

IR (liquid film): 3410, 2930, 2850, 1722, 1650, 1130, 1020 and 972 cm⁻¹.

NMR (deuterochloroform solution): δ= 6.87 (1H, dt), 5.67 (1H, d), 5.31 (2H, m), 4.65 (2H, m), 3.71 (3H, s), 4.13-3.22 (7H, m).

TLC (developing solvent; cyclohexane:ethyl acetate = 2:1): Rf = 0.35.

EXAMPLE 26

Methyl 9α-hydroxy-11α,15α-bis-(2-tetrahydropyranyloxy)-16(R)-methylprosta-trans-2,-cis-5,trans-13-trienoate By the same procedure as described in Example 22, 173 mg. of the title compound were obtained from 550 mg. of methyl 9α-hydroxy-11α,15α-bis-(2-tetrahydropyranyloxy)-16(R)-methylprosta-cis-5,trans-13-dienoate [cf. Reference Example 2(e)].

IR (liquid film): 3420, 2920, 2830, 1723, 1650, 1130, 1020 and 977 cm⁻¹.

NMR (deuterochloroform solution): δ= 6.96 (1H, dt), 5.83 (1H, dt), 5.65-5.30 (4H, m), 4.65 (2H, m), 3.69 (3H, s), 4.16-3.35 (7H, m), 3.00 (2H, t).

TLC (development solvent; cyclohexane:ethyl acetate = 2:1): Rf = 0.36.

EXAMPLE 27

Methyl 9α-hydroxy-11α,15-bis-(2-tetrahydropyranlyloxy)17-methylprosta-trans-2,trans-13-dienoate By the same procedure as described in Example 22, 179 mg. of the title compound were obtained from 552 mg. of methyl 9α-hydroxy-11α,15-bis-(2-tetrahydropyranyloxy)-17-methylprost-trans-13-enoate [cf. Reference Example 2(f)].

IR (liquid film): 3420, 2920, 2820, 1725, 1650, 1130, 1020 and 974 cm⁻¹.

NMR (deuterochloroform solution): δ=6.87 (1H, dt), 5.66 (1H, d), 5.50-5.25 (2H, m), 4.60 (2H, m), 3.70 (3H, s), 4.12-3.25 (7H, m).

TLC (developing solvent; cyclohexane:ethyl acetate = 2:1): Rf = 0.35.

EXAMPLE 28

Methyl 9α-hydroxy-11α,15-bis-(2-tetrahydropyranyloxy)-17-methylprosta-trans-2,cis-5,-trans-13-trienoate By the same procedure as described in Example 22, 167 mg. of the title compound were obtained from 550 mg. of methyl 9α-hydroxy-11α,15-bis-(2-tetrahydropyranyloxy)-17-methylprosta-cis-5,trans-13-dienoate [cf. Reference Example 2(g)].

IR (liquid film): 3420, 2920, 2820, 1725, 1650, 1130, 1020 and 977 cm⁻¹.

NMR (deuterochloroform solution): δ=6.95 (1H, dt), 6.83 (1H, dt), 5.67-5.33 (4H, m), 4.65 (2H, m), 3.70 (3H, s), 4.16-3.32 (7H, n), 2.98 (2H, t).

TLC (developing solvent; cyclohexane:ethyl acetate = 2:1): Rf = 0.36.

EXAMPLE 29

Methyl 9α-hydroxy-11α,15-bis-(2-tetrahydropyranyloxy)-15,16-dimethylprosta-trans-2,trans-13-dienoate By the same procedure as described in Example 22, 183 mg. of the title compound were obtained from 566 mg. of methyl 9α-hydroxy-11α,15-bis-(2-tetrahydropyranyloxy)-15,16-dimethylprost-trans-13-enoate [cf. Reference Example 2(h)].

IR (liquid film): 3450, 2920, 2830, 1720, 1650, 1120, 1020 and 979 cm⁻¹.

NMR (deuterochloroform solution): δ=6.87 (1H, dt), 5.68 (1H, d), 5.70-5.30 (2H, m), 4.64 (2H, m), 3.69 (3H, s), 4.15-3.27 (6H, m).

TLC (developing solvent; cyclohexane:ethyl acetate = 2:1): Rf = 0.38.

EXAMPLE 30

Methyl
9α-hydroxy-11α,15-bis-(2-tetrahydropyranyloxy)-15,16-dimethylprosta-trans-2,cis-5,trans-13-trienoate By the same procedure as described in Example 22, 180 mg. of the title compound were obtained from 564 mg. of methyl 9α-hydroxy-11α,15-bis-(2-tetrahydropyranyloxy)-15,16-dimethylprosta-cis-5,trans-13-dienoate [cf. Reference Example 2(i)].

IR (liquid film): 3430, 2920, 2830, 1720, 1652, 1130, 1020 and 978 cm$^{-1}$.

NMR (deuterochloroform solution): $\delta$=6.96 (1H, dt), 5.81 (1H, dt), 5.67-5.35 (4H, m), 4.65 (2H, m), 3.70 (3H, s), 4.15-3.36 (6H, m), 3.01 (2H, t).

TLC (developing solvent; cyclohexane:ethyl acetate = 2:1): Rf = 0.39.

EXAMPLE 31

Methyl
9α-hydroxy-11α,15-bis-(2-tetrahydropyranyloxy)-16-phenyl-ω-trinorprosta-trans-2,trans-13-dienoate By the same procedure as described in Example 22, 185 mg. of the title compound were obtained from 572 mg. of methyl 9α-hydroxy-11α,15-bis-(2-tetrahydropyranyloxy)-16-phenyl-ω-trinorprost-trans-13-enoate [cf. Reference Example 2(j)].

IR (liquid film): 3450, 3030, 2940, 1720, 1650, 1023 and 690 cm$^{-1}$.

NMR (deuterochloroform solution): $\delta$=7.12 (5H, m), 6.87 (1H, dt), 5.69 (1H, d), 5.50-5.20 (2H, m), 4.61 (2H, m), 3.72 (3H, s), 4.10-3.20 (7H, m).

TLC (developing solvent; cyclohexane:ethyl acetate = 2:1): Rf = 0.37.

EXAMPLE 32

Methyl
9α-hydroxy-11α,15-bis-(2-tetrahydropyranyloxy)-16-phenyl-ω-trinorprosta-trans-2,cis-5,-trans-13-trienoate By the same procedure as described in Example 22, 179 mg. of the title compound were obtained from 570 mg. of methyl 9α-hydroxy-11α,15-bis-(2-tetrahydroxypyranyloxy)-16-phenyl-ω-trinorprosta-cis-5,trans-13-dienoate [cf. Reference Example 2(k)].

IR (liquid film): 3440, 3030, 2940, 1720, 1650, 1023, and 692 cm$^{-1}$.

NMR (deuterochloroform solution): $\delta$=7.13 (5H, m), 6.88 (1H, dt), 5.70 (1H, dt), 5.68-5.35 (4H, m), 4.62 (2H, m), 3.71 (3H, s), 4.16-3.35 (7H, m), 3.01 (2H, t). TLC (developing solvent; cyclohexane:ethyl acetate = 2:1): Rf = 0.38.

EXAMPLE 33

Methyl
9α-hydroxy-11α,15α-bis-(2-tetahydropyranyloxy)-16-cyclohexyl-ω-trinorprosta-trans-2,trans-13-dienoate By the same procedure as described in Example 22, 187 mg. of the title compound were obtained from 578 mg. of methyl 9α-hydroxy-11α,15α-bis-(2-tetrahydropyranyloxy)-16-cyclohexyl-ω-trinorprost-trans-13-enoate [cf. Reference Example 2(l)].

IR (liquid film): 3440, 2900, 2820, 1720, 1651, 1120, 1020 and 901 cm$^{-1}$.

NMR (deuterochloroform solution): $\delta$=6.84 (1H, dt), 5.65 (1H, d), 5.50-5.20 (2H, m), 4.61 (2H, m), 3.68 (3H, s), 4.10-3.20 (7H, m).

TLC (developing solvent; cyclohexane:ethyl acetate = 2:1): Rf = 0.40.

EXAMPLE 34

Methyl
9α-hydroxy-11α,15α-bis-(2-tetrahydropyranyloxy)-16-cyclohexyl-ω-trinor-prosta-trans-2,cis-5,trans-13-trienoate By the same procedure as described in Example 22, 182 mg. of the title compound were obtained from 576 mg. of methyl 9α-hydroxy-11α,15α-bis(2-tetrahydropyranyloxy)-16-cyclohexyl-ω-trinorprosta-cis-5,trans-13-dienoate [cf. Reference Example 2(m)].

IR (liquid film): 3440, 2920, 2820, 1720, 1650, 1120, 1020 and 901 cm$^{-1}$.

NMR (deuterochloroform solution): $\delta$=6.95 (1H, dt), 5.82 (1H, dt), 5.67-5.35 (4H, m), 4.66 (2H, m), 3.70 (3H, s), 4.16-3.31 (7H, m), 2.98 (2H, t).

TLC (developing solvent; cyclohexane:ethyl acetate = 2:1): Rf = 0.42.

By procedures described in the specification of United States Patent Application 427,403 the products of Examples 21, 25 and 27 were converted to trans-$\Delta^2$-PGF$_{1\alpha}$, trans-$\Delta^2$-PGE$_1$, trans-$\Delta^2$-PGA$_1$, 16(R)-methyl-trans-$\Delta^2$-PGF$_{1\alpha}$; 17-methyl-trans-$\Delta^2$-PGF$_{1\alpha}$ and 17-methyl-trans-$\Delta^2$-PGE$_1$. Also the products of Examples 23, 29, 31 and 33 were converted using procedures described in the aforesaid application to 15-methyl-trans-$\Delta^2$-PGF$_{1\alpha}$, 15-methyl-trans-$\Delta^2$-PGE$_1$, 15-methyl-trans-$\Delta^2$-PGA$_1$, 15,16-dimethyl-trans-$\Delta^2$-PGF$_{1\alpha}$, 15,16-dimethyl-trans-$\Delta^2$-PGE$_1$, 15,16-dimethyl-trans-$\Delta^2$-PGA$_1$, 16-phenyl-ω-trinor-trans-$\Delta^2$-PGF$_{1\alpha}$, 16-phenyl-ω-trinor-trans-$\Delta^2$-PGE$_1$, 16-phenyl-ω-trinor-trans-$\Delta^2$-PGA$_1$, 16-cyclohexyl-ω-trinor-trans-$\Delta^2$PGE$_1$ and 16-cyclohexyl-ω-trinor-trans-$\Delta^2$-PGA$_1$, respectively.

Furthermore, the products of Examples 22, 24, 26, 28, 30, 32 and 34 were converted to trans-$\Delta^2$-PGF$_{2\alpha}$ methyl ester, trans-$\Delta^2$-PGE$_2$ methyl ester, trans-$\Delta^2$-PGA$_2$ methyl ester, 15-methyl-trans-$\Delta^2$-PGF$_{2\alpha}$ methyl ester, 15-methyl-trans-$\Delta^2$-PGE$_2$ methyl ester, 15-methyl-trans-$\Delta^2$-PGA$_2$ methyl ester, 16(R)-methyl-trans-$\Delta^2$-PGF$_{2\alpha}$ methyl ester, 16(R)-methyl-trans-$\Delta^2$-PGE$_2$ methyl ester, 16(R)-methyl-trans-$\Delta^2$-PGA$_2$ methyl ester, 17-methyl-trans-$\Delta^2$-PGF$_{2\alpha}$ methyl ester, 17-methyl-trans-$\Delta^2$-PGE$_2$ methyl ester, 17-methyl-trans-$\Delta^2$-PGA$_2$ methyl ester, 15,16-dimethyl-trans-$\Delta^2$-PGF$_{2\alpha}$ methyl ester, 15,16-dimethyl-trans-$\Delta^2$-PGE$_2$ methyl ester, 15,16-dimethyl-trans-$\Delta^2$-PGA$_2$ methyl ester, 16-phenyl-ω-trinor-trans-$\Delta^2$PGF$_{2\alpha}$ methyl ester, 16-phenyl-ω-trinor-trans-$\Delta^2$-PGE$_2$ methyl ester, 16-phenyl-ω-trinor-trans-$\Delta^2$-PGA$_2$ methyl ester, 16-cyclohexyl-ω-trinor-trans-$\Delta^2$-PGF$_{2\alpha}$ methyl ester, 16-cyclohexyl-ω-trinor-trans-$\Delta^2$-PGE$_2$ methyl ester and 16-cyclohexyl-ω-trinor-trans-$\Delta^2$-PGA$_2$ methyl ester by application of procedures described in foregoing Examples 15 to 20.

The methyl esters of these trans-$\Delta^2$-PG-2 compounds were converted to the corresponding PG-2 acids, viz. trans-$\Delta^2$-PGF$_{2\alpha}$, trans-$\Delta^2$-PGE$_2$, trans-$\Delta^2$-PGA$_2$, 15-methyl-trans-$\Delta^2$-PGF$_{2\alpha}$, 15-methyl-trans-$\Delta^2$-PGE$_2$, 15-methyl-trans-$\Delta^2$-PGA$_2$, 16(R)-methyl-trans-$\Delta^2$-PGF$_{2\alpha}$, 16(R)-methyl-trans-$\Delta^2$-PGE$_2$, 16(R)-methyl-trans-$\Delta^2$-PGA$_2$, 17-methyl-trans-$\Delta^2$-PGF$_{2\alpha}$, 17-methyl-trans-$\Delta^2$-PGE$_2$, 17-methyl-trans-$\Delta^2$-PGA$_2$, 15,16-dimethyl-trans-$\Delta^2$-PGF$_{2\alpha}$, 15,16-dimethyl-trans-$\Delta^2$-PGE$_2$, 15,16-dimethyl-trans-$\Delta^2$-PGA$_2$, 16-phenyl-ω-trinor-trans-$\Delta^2$-PGF$_{2\alpha}$, 16-phenyl-ω-trinor-trans-$\Delta^2$-PGE$_2$, 16-phenyl-ω-trinor-trans-$\Delta^2$-PGA$_2$, 16-cyclohexyl-ω-trinor-trans-$\Delta^2$-PGF$_{2\alpha}$, 16-cyclohexyl-ωtrinor-trans-$\Delta^2$-PGE$_2$ and 16-cyclohexyl-ω-trinor-trans-$\Delta^2$-PGA$_2$, by treatment with baker's yeast.

In the foregoing Examples and compounds mentioned in the accompanying claims where the configuration of a radical or group is unspecified, it is to be understood that in the case of tetrahydropyranyloxy groups and hydroxy groups obtained from such tetrahydropyranyloxy groups the configuration is α or β or a mixture of α-and β-configurations, or in the case of methyl radicals or phenyl or cyclohexyl radicals the configuration is R or S or a mixture of R- and S-configurations.

The present invention includes within its scope pharmaceutical compositions which comprise at least one new therapeutically useful prostaglandin compound of general formula XXXIV or a cyclodextrin clathrate or, when $R^{3'}$ represents a hydrogen atom, a non-toxic salt thereof, or a prostaglandin alcohol of general formula XXXVIII wherein Y represents cis-vinylene or a cyclodextrin clathrate thereof, together with a pharmaceutical carrier or coating. In clinical practice the new compounds of the present invention will normally be administered orally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solution, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming, and preserving agents. The compositions according to the invention, for oral administration also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compoositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.01 and 5 mg./kg. body weight by oral administration in the treatment of hypertension, between 0.5 and 100 μg./kg. body weight by oral administration in the treatment of gastric ulceration, between 0.1 and 50 μg./kg. body weight by aerosol administration in the treatment of asthma, between 0.01 and 5 mg./kg. body weight by oral administration in the treatment of disorders of the peripheral circulation, and between 0.01 and 5 mg./kg. body weight by oral administration in the prevention and treatment of cerebral thrombosis and myocardial infarction and, in respect of the prostaglandin compounds of general formula XXXIV and, when $R^{3'}$ represents a hydrogen atom, non-toxic salts thereof, between 0.1 and 100 mg. per day by oral administration in the treatment of autoimmune conditions.

Prostaglandin according to the present invention may be administered orally as bronchodilators by any method known per se for administration by insulation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the valatile liquid propellant is between about 25 and 65 pounds, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredients in the co-solvent or combining the required quantity of active ingredient with a measured quantity of suspending or dispersing agent. A measured quantity of this composition is then placed in an open container which is to be used as the pressurized pack. The container and its contents are the cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg., of active ingredient per ml. of solution or suspension. It is important that the pH of solutions and suspensions used, according to the present invention, to generate aerosols should be kept within the range 3 to 8 and preferable that they should be stored at or below 4° C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 35

16(R)-Methyl-trans-$\Delta^2$-PGE$_2$ (500 $\mu$g.) was dissolved in ethanol (1 ml.) and the solution obtained was added to an aqueous solution (12 ml.) containing sodium carbonate (50 mg.). Aqueous sodium chloride solution (0.9 w/v, 2 ml.) was then added to give a final volume of 15 ml. The solution was then sterilized by passage through a bacteria-retaining filter and placed in 1.5 ml. portions in 5 ml. ampoules, to give 50 $\mu$g. of 16 (R)-methyl-trans-$\Delta^2$-PGE$_2$ (in the form of its sodium salt) per ampoule. The contents of the ampoules were freeze-dried and the ampoules sealed. The contents of an ampoule in a suitable volume, e.g. 2 ml., of sterile water or physiological saline, gave a solution ready for administration by injection.

EXAMPLE 36 trans-$\Delta^2$-PGA$_2$ methyl ester (20 mg.) was dissolved in ethanol (10 ml.), mixed with mannitol (18.5 g.), sieved through a 30-mesh sieve, dried at 30° C. for 90 minutes and again seived through a 30-mesh sieve. Aerosil (microfine silica; 200 mg.) was added and the powder obtained was machine-filled into one hundred No. 2 hard gelatin capsules to give capsules each containing 200$\mu$g. of trans-$\Delta^2$-PGA$_2$ methyl ester, which after swallowing of the capsule is released into the stomach.

We claim:

1. A compound of the formula:

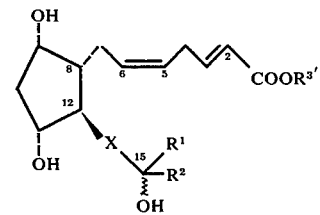

wherein R$_1$ represents an alkyl group containing from 1 to 10 carbon atoms, or an alkyl group containing from 1 to 6 carbon atoms carrying a phenyl substituent or a cycloalkyl substituent of 5 to 7 carbon atoms, R$_2$ represents a hydrogen atom or an alkyl group containing from 1 to 4 carbon atoms, X represents ethylene or trans-vinylene, and R$^{3'}$ represents a hydrogen atom or an alkyl group containing from 1 to 12 carbon atoms, the double bonds in the 2- and 5-positions being in the trans- and cis-configurations respectively, and cyclodextrin clathrates thereof, and non-toxic salts of the acids wherein R³ represents a hydrogen atom.

2. A compound according to claim 1 in which

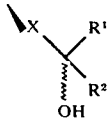

is a grouping of the formula:

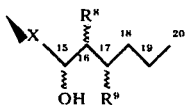

wherein R⁸ and R⁹ which may be the same or different each represent a hydrogen atom or a methyl group.

3. A compound according to claim 1 in which

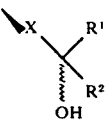

in a grouping of the formula:

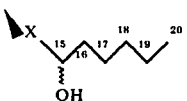

wherein the carbon atom in the 15-position carries a methyl group, or the carbon atoms in the 15- and 16-positions each carry a methyl group.

4. A compound according to claim 1 in which

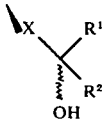

in a grouping of the formula:

wherein $R^{10}$ represents a phenyl or cyclohexyl radical.

5. A compound according to claim 1 wherein X represents trans-vinylene.

6. A compound according to claim 1 which is trans-$\Delta^2 PGF_{2\alpha}$ and the methyl ester thereof.

7. A compound according to claim 1 which is 15-methyl-trans-$\Delta^2$-$PGF_{2\alpha}$ and the methyl ester thereof.

8. A compound according to claim 1 which is 16-methyl-trans-$\Delta^2$-$PGF_{2\alpha}$ and the methyl ester thereof.

9. A compound according to claim 1 which is 16(R)-methyl-trans-$\Delta^2$-$PGF_{2\alpha}$ and the methyl ester thereof.

10. A compound according to claim 1 which is 17-methyl-trans-$\Delta^2$-$PGF_{2\alpha}$ and the methyl ester thereof.

11. A compound according to claim 1 which is 15,16-dimethyl-trans-$\Delta^2$-$PGF_{2\alpha}$ and the methyl ester thereof.

12. A compound according to claim 1 which is 16-phenyl-ω-trinor-trans-$\Delta^2$-$PGF_{2\alpha}$ and the methyl ester thereof.

13. A compound according to claim 1 which is 16-cyclohexyl-ω-trinor-trans-$\Delta^2$-$PGF_{2\alpha}$ and the methyl ester thereof.

* * * * *

UNITED STATES PATENT OFFICE
CERTIFICATE OF CORRECTION

PATENT NO. : 4,024,174
DATED : May 17, 1977
INVENTOR(S) : MASAKI HAYASHI, ET AL.

It is certified that error appears in the above-identified patent and that said Letters Patent are hereby corrected as shown below:

On the cover page, the filing date is shown as Dec. 19, 1964, whereas it was filed Dec. 19, 1974.

Signed and Sealed this ninth Day of August 1977

[SEAL]

Attest:

RUTH C. MASON
Attesting Officer

C. MARSHALL DANN
Commissioner of Patents and Trademarks